United States Patent
Matsuo et al.

(10) Patent No.: US 12,202,869 B2
(45) Date of Patent: Jan. 21, 2025

(54) INHIBITION OF MYOSTATIN SIGNAL BY MYOSTATIN SPLICE VARIANT-DERIVED PROTEIN AND UTILIZATION THEREOF

(71) Applicants: KNC LABORATORIES CO., LTD., Hyogo (JP); Kobe Gakuin Educational Foundation, Hyogo (JP)

(72) Inventors: Masafumi Matsuo, Hyogo (JP); Kosuke Okazaki, Hyogo (JP); Kazuhiro Maeta, Hyogo (JP)

(73) Assignee: KNC LABORATORIES CO., LTD., Hyogo (JP)

( * ) Notice: Subject to any disclaimer, the term of this patent is extended or adjusted under 35 U.S.C. 154(b) by 571 days.

(21) Appl. No.: 17/435,215

(22) PCT Filed: Feb. 26, 2020

(86) PCT No.: PCT/JP2020/007671
§ 371 (c)(1),
(2) Date: Aug. 31, 2021

(87) PCT Pub. No.: WO2020/179571
PCT Pub. Date: Sep. 10, 2020

(65) Prior Publication Data
US 2022/0135637 A1 May 5, 2022

(30) Foreign Application Priority Data
Mar. 1, 2019 (JP) .................. 2019-037915

(51) Int. Cl.
- C07K 14/495 (2006.01)
- A23K 20/147 (2016.01)
- A23L 33/18 (2016.01)
- A61K 38/00 (2006.01)

(52) U.S. Cl.
CPC .......... *C07K 14/495* (2013.01); *A23K 20/147* (2016.05); *A23L 33/18* (2016.08); *A23V 2002/00* (2013.01); *A61K 38/00* (2013.01)

(58) Field of Classification Search
CPC ..... C07K 14/495; A23K 20/147; A23L 33/18; A23V 2002/00; A61K 38/00
See application file for complete search history.

(56) References Cited

FOREIGN PATENT DOCUMENTS

WO   WO-2010134686 A2 * 11/2010 ........... A23K 20/147

OTHER PUBLICATIONS

Myostatin, partial [synthetic construct], from https://www.ncbi.nlm.nih.gov/protein/ABZ92482.1?report=genbank&log$=protalign&blast_rank=2&RID=XCHDJJWN013, 2016, pp. 1-2.*
Macine translation of WO 2010134686 A2, pp. 1-12, accessed Apr. 4, 2024.*
SEQ ID No. 8 in WO 2010134686 A2, pp. 1-2, accessed Apr. 4, 2024.*
Myostatin-b [*Homo sapiens*], from https://www.ncbi.nlm.nih.gov/protein/UQT28931.1?report=genbank&log$=protalign&blast_rank=1&RID=0VEYM05B016, 2022, p. 1.*
Drumm et al., Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
Muscle Atrophy, from https://my.clevelandclinic.org/health/diseases/22310-muscle-atrophy, 2022, pp. 1-10.*
Myostatin-related muscle hypertrophy, from https://rarediseases.info.nih.gov/diseases/10238/myostatin-related-muscle-hypertrophy, 2024, pp. 1-14.*
Lee et al, Challenges and Future Prospects of Targeting Myostatin/Activin A Signaling to Treat Diseases of Muscle Loss and Metabolic Dysfunction, Gerontol A Biol Sci Med Sci, 2023, 78, pp. S32-S37.*
International Search Report issued May 19, 2020 in International (PCT) Application No. PCT/JP2020/007671.

* cited by examiner

*Primary Examiner* — Li N Komatsu
(74) *Attorney, Agent, or Firm* — Wenderoth, Lind & Ponack, L.L.P.

(57) ABSTRACT

A method of inhibiting myostatin signaling via a myostatin splice variant-derived protein is provided. The protein and an expression system thereof are applicable to therapy for diseases in which myostatin is involved.

6 Claims, 6 Drawing Sheets

Specification includes a Sequence Listing.

INHIBITION OF MYOSTATIN SIGNAL BY MYOSTATIN SPLICE VARIANT-DERIVED PROTEIN AND UTILIZATION THEREOF

SEQUENCE LISTING

A sequence listing in electronic (ASCII text file) format is filed with this application and incorporated herein by reference. The name of the ASCII text file is "2021-0873A_ST25.txt"; the file was created on Aug. 6, 2024; the size of the file is 16,012 bytes.

TECHNICAL FIELD

The present invention relates to inhibition of myostatin signaling by a myostatin splice variant-derived protein and use thereof.

BACKGROUND ART

Myostatin is produced in cells as a precursor, which is converted into mature myostatin upon cleavage by protease. When this mature myostatin binds to its receptor on cell surfaces, Smad2/3 is phosphorylated and the phosphorylated Smad2/3 transits into the nucleus. The phosphorylated Smad2/3 then binds to an Smad binding element present in the promoter of a target gene, whereupon expression of the target gene is induced (myostatin signaling). Activation of myostatin signaling induces gene expression, and the induced factor negatively regulates myogenesis. In contrast, inhibition of myostatin signaling promotes myogenesis. Since promotion of myogenesis is applicable to treatment of amyotrophic diseases such as muscular dystrophy, inhibition of myostatin signaling is believed to be a potential therapy for muscle atrophy (Non-Patent Document No. 1). Moreover, decrease in myostatin expression inhibits cancer cell proliferation (Non-Patent Document No. 2). These results suggest that decrease in myostatin level and inhibition of myostatin signaling are effective in cancer treatment. Further, since expression levels of myostatin are elevated in type 2 diabetes patients, it is thought that there is some relation between myostatin and diabetes (Non-Patent Document No. 3). From what have been described above, it is believed that inhibition of myostatin signaling would be effective for suppression of diabetes or inhibition of its progression.

As a method of inhibiting myostatin signaling, use of a peptide that binds to myostatin has been examined. This peptide is derived from a sequence that myostatin per se has and was actually capable of inhibiting myostatin signaling. However, this peptide has a problem of low stability upon administration into a living body (Non-Patent Document No. 4; Patent Document No. 1).

Further, a method of inhibiting myostatin signaling using a sheep myostatin splice variant has also been reported (Non-Patent Document No. 5; Patent Document No. 2). However, nothing equivalent to the myostatin splice variant found in sheep has been discovered in human.

PRIOR ART LITERATURE

Non-Patent Documents

Non-Patent Document No. 1: Bogdanovich et al., Nature, 2002, 420; 418-421
Non-Patent Document No. 2: Han et al., Redox Biol. 2018, 19; 412-4128
Non-Patent Document No. 3: Palsgaard et al. 2009, 4; e6575
Non-Patent Document No. 4: Ohsawa et al., PlosOne, 2015, 10; e0133713
Non-Patent Document No. 5: Jeanplong et al., PlosOne, 2013, 8; e81713

Patent Documents

Patent Document No. 1: WO2014/119753A1
Patent Document No. 2: WO2006/036074A1

DISCLOSURE OF THE INVENTION

Problem for Solution by the Invention

It is an object of the present invention to provide a method of inhibiting myostatin signaling.

Means to Solve the Problem

As a result of intensive and extensive researches, the present inventors have found that a protein translated from a myostatin splice variant (a variant produced by changes in splicing pattern) inhibits myostatin signaling. The protein translated from the mRNA of the myostatin splice variant does not have the active region required for mature myostatin, but retains more than 90% of the prodomain (FIG. 3). It was possible to inhibit myostatin signaling by allowing overexpression of the myostatin variant in cultured cells (FIG. 6). Since the protein translated from the myostatin splice variant is a protein naturally produced in vivo, it is believed to have better stability than exogenous proteins. By inhibiting myostatin signaling, treatment of amyotrophic diseases due to promotion of myogenesis becomes possible. Moreover, inhibition of cancer cell proliferation by inhibition of myostatin signaling also becomes possible. Further, activation of myostatin signaling associated with myostatin increase is suggested to be potentially related to diabetes, so it is believed that inhibition of myostatin signaling is effective for preventing diabetes or for inhibiting its progression. Therefore, this protein and an expression system thereof are applicable to therapy for diseases in which myostatin is involved.

A summary of the present invention is described as below.
(1) A protein of the following (a) or (b):
  (a) a protein comprising the amino acid sequence as shown in SEQ ID NO: 1
  (b) a protein comprising an amino acid sequence having at least 70% or more sequence identity with the amino acid sequence as shown in SEQ ID NO: 1 and which yet is capable of inhibiting myostatin signaling.
(2) A polynucleotide comprising a nucleotide sequence encoding the protein of (1) above or a sequence complementary to the nucleotide sequence.
(3) A vector comprising the polynucleotide of (2) above.
(4) A cell comprising the vector of (3) above.
(5) A method of preparing a protein of the following (a) or (b), comprising culturing the cell of (4) above:
  (a) a protein comprising the amino acid sequence as shown in SEQ ID NO: 1
  (b) a protein comprising an amino acid sequence having at least 70% or more sequence identity with the amino acid sequence as shown in SEQ ID NO: 1 and which yet is capable of inhibiting myostatin signaling.

(6) A composition for inhibiting myostatin signaling, comprising at least one member selected from the group consisting of the protein of (1), the polynucleotide of (2), the vector of (3) and the cell of (4).

(7) A composition for promoting myogenesis, comprising at least one member selected from the group consisting of the protein of (1), the polynucleotide of (2), the vector of (3) and the cell of (4).

(8) A composition for preventing and/or treating a disease in which myostatin is involved, comprising at least one member selected from the group consisting of the protein of (1), the polynucleotide of (2), the vector of (3) and the cell of (4).

(9) A pharmaceutical drug comprising at least one member selected the group consisting of the protein of (1), the polynucleotide of (2), the vector of (3) and the cell of (4).

(10) A food comprising at least one member selected from the group consisting of the protein of (1), the polynucleotide of (2), the vector of (3) and the cell of (4).

(11) A feed comprising at least one member selected from the group consisting of the protein of (1), the polynucleotide of (2), the vector of (3) and the cell of (4).

(12) A method for preventing and/or treating a disease in which myostatin is involved, comprising administering to a subject a pharmaceutically effective amount of at least one member selected from the group consisting of the protein of (1), the polynucleotide of (2), the vector of (3) and the cell of (4).

(13) At least one member selected from the group consisting of the protein of (1), the polynucleotide of (2), the vector of (3) and the cell of (4) for use in a method of preventing and/or treating a disease in which myostatin is involved.

Effect of the Invention

It is possible to inhibit myostatin signaling with a protein translated from a myostatin splice variant.

The present specification encompasses the contents disclosed in the specification and/or the drawings of Japanese Patent Application No. 2019-37915 based on which the present patent application claims priority.

This figure shows the results of PCR amplification of a myostatin (MSTN) gene product of human rhabdomyosarcoma cells. Two amplification products were obtained by PCR (MSTN and MSTN-V) (left panel). Nucleotide sequences of respective products were analyzed to thereby obtain exon structures, which are schematically shown in the right panel. The nucleic acid sequence above the exon structure of MSTN (left side) is SEQ ID NO: 8. The nucleic acid sequence above the exon structure of MSTN (right side) is SEQ ID NO: 9. The nucleic acid sequence below the exon structure of MSTN-V is SEQ ID NO: 10. In MSTN-V, nucleotides from No. 881 to No. 1843 in MSTN are missing. The sequence of the junction site between exon 2 and exon 3 for each product is shown, together with part of the nucleotide sequence starting from nucleotide No. 1844 (right lower panel) where the nucleic acid sequences for MSTN are SEQ ID NOs: 8 and 9, from left to right, and the nucleic acid sequence for MSTN-V is SEQ ID NO: 10.

Figure 2:
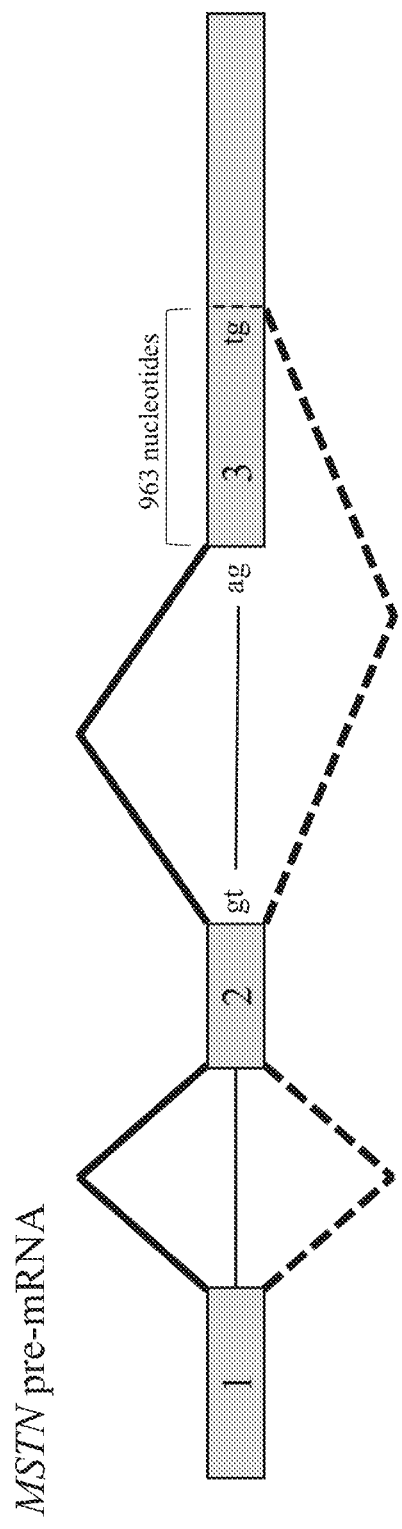

FIG. 2 Splicing of Myostatin Gene

MSTN is composed of exon 1, exon 2 and exon 3 (solid line) that remain after introns 1 and 2 have been spliced from pre-mRNA of MSTN gene. Intron 2 is the most common intron having GT sequence and AG sequence at 5' end and 3' end, respectively. On the other hand, the mode of splicing of intron 2 is different in MSTN-V; TG in exon 3 (which is a cryptic splice acceptor site) is activated to thereby form a GT-TG intron (dotted line). As a result, 963 nucleotides spanning from nucleotide No. 881 to No. 1843 in exon 3 are deleted in myostatin V.

Figure 3:
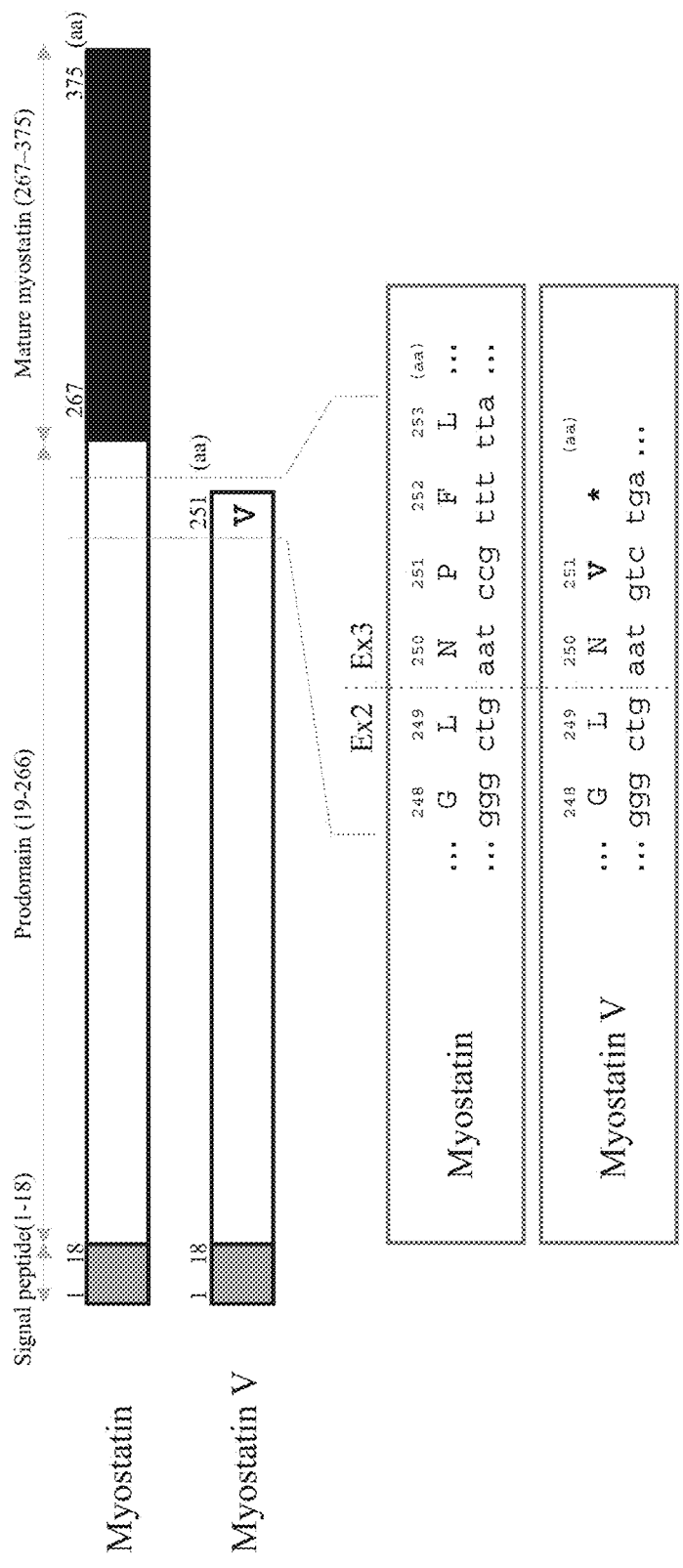

FIG. 3 Myostatin V Protein

Protein structures of myostatin and myostatin V are shown schematically. Myostatin is composed of signal peptide (nucleotide No. 1 to No. 18), prodomain (nucleotide No. 19 to No. 266) and mature myostatin (nucleotide No. 267 to No. 375) in this order from N terminus. Nucleotide sequences of myostatin and myostatin V are identical in exon 1 and exon 2, with commonality of up to amino acid No. 249. Since myostatin V is different in the nucleotide sequence of exon 3, the $250^{th}$ amino acid from N terminus is asparagine (N), the $251^{st}$ amino acid is valine (V) and the $252^{nd}$ position is stop codon (*) (SEQ ID NO: 1). For this reason, myostatin V does not have the domain of mature myostatin. The amino acid and nucleic acid sequences shown for Myostatin are SEQ ID NOs. 11 and 12, respectively. The amino acid and nucleic acid sequences shown for Myostatin V are SEQ ID NOs. 13 and 14, respectively.

Figure 4:
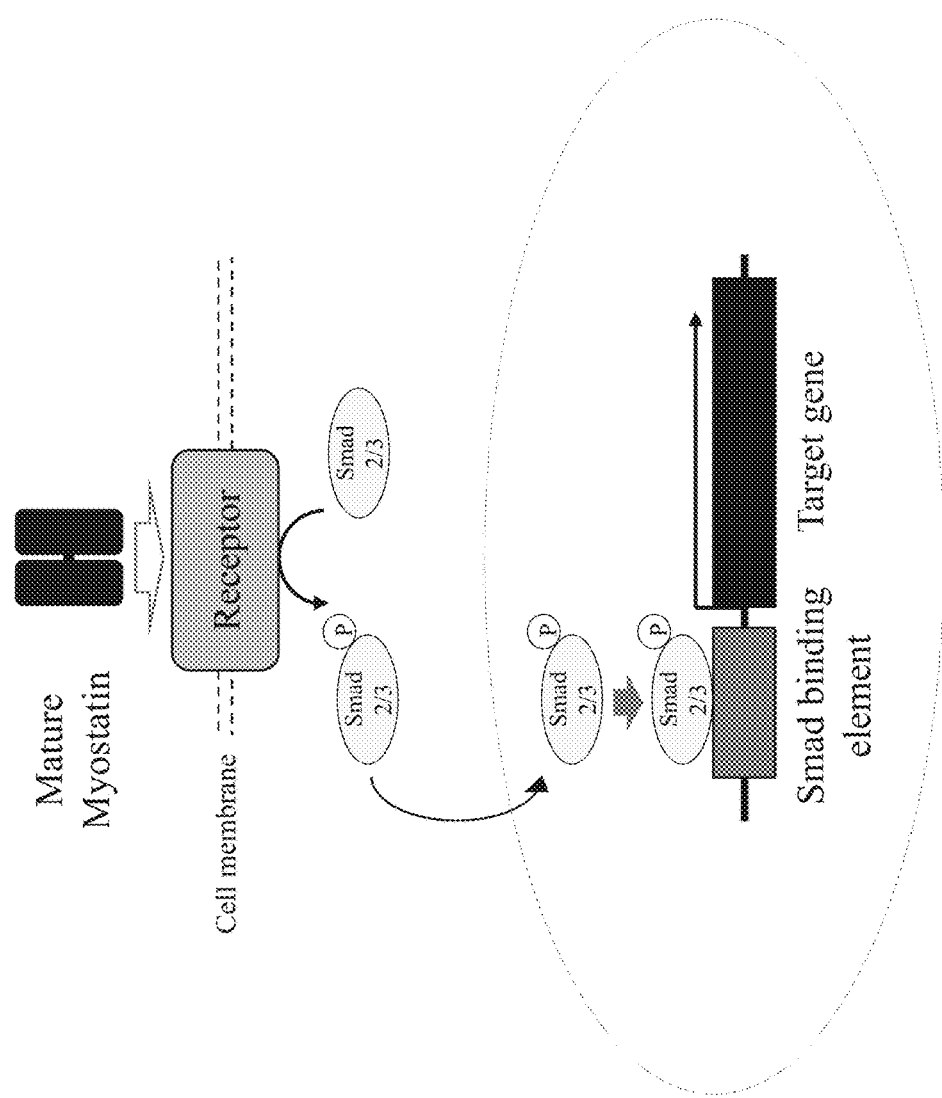

FIG. 4 Myostatin Signaling

Mature myostatin generated from precursor binds to its receptor on cell surfaces to thereby activate downstream signal transduction. When mature myostatin binds to its receptor, Smad2/3 is phosphorylated and the phosphorylated Smad2/3 transits into the nucleus. The phosphorylated Smad2/3 then binds to an Smad binding element present in the promoter of a target gene, whereupon expression of the target gene is induced.

Figure 5:
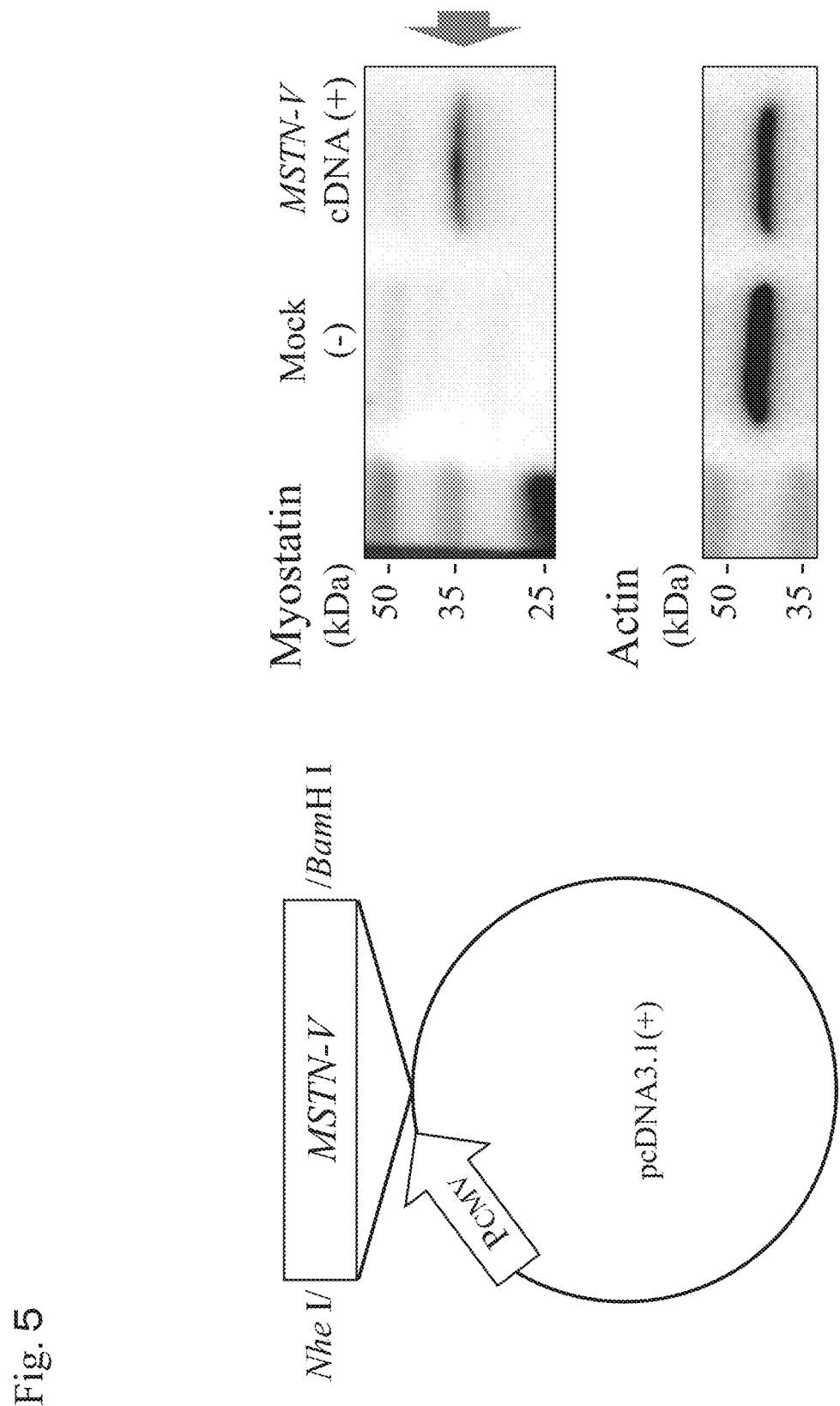

FIG. 5 Myostatin V Expression Vector and Expressed Protein

MSTN-V expression vector was prepared as described below. Briefly, an artificial synthetic nucleic acid was prepared by adding Nhe I recognition sequence (GCTTGC) to 5' end and BamH I recognition sequence (GGATCC) to 3' end of SEQ ID NO: 3, a sequence optimized for codon usage frequency with respect to SEQ ID NO: 2. The synthetic nucleic acid was inserted into the Nhe I/BamH I recognition site of pcDNA™3.1 (+) vector to thereby prepare MSTN-V expression vector (left panel). The thus prepared vector was introduced into myocytes, and the expressed protein was analyzed by Western blotting. A specific band was detected at around a molecular weight of 35 kDa (arrow mark) in the sample extracted from MSTN-V expression vector-introduced cells, and expression of myostatin V was confirmed (right panel). The left lane represents molecular weight marker; the middle lane represents "Mock" (sample derived from empty vector-introduced cells); and the right lane represents sample derived from MSTN-V expression vector-introduced cells.

Figure 6:
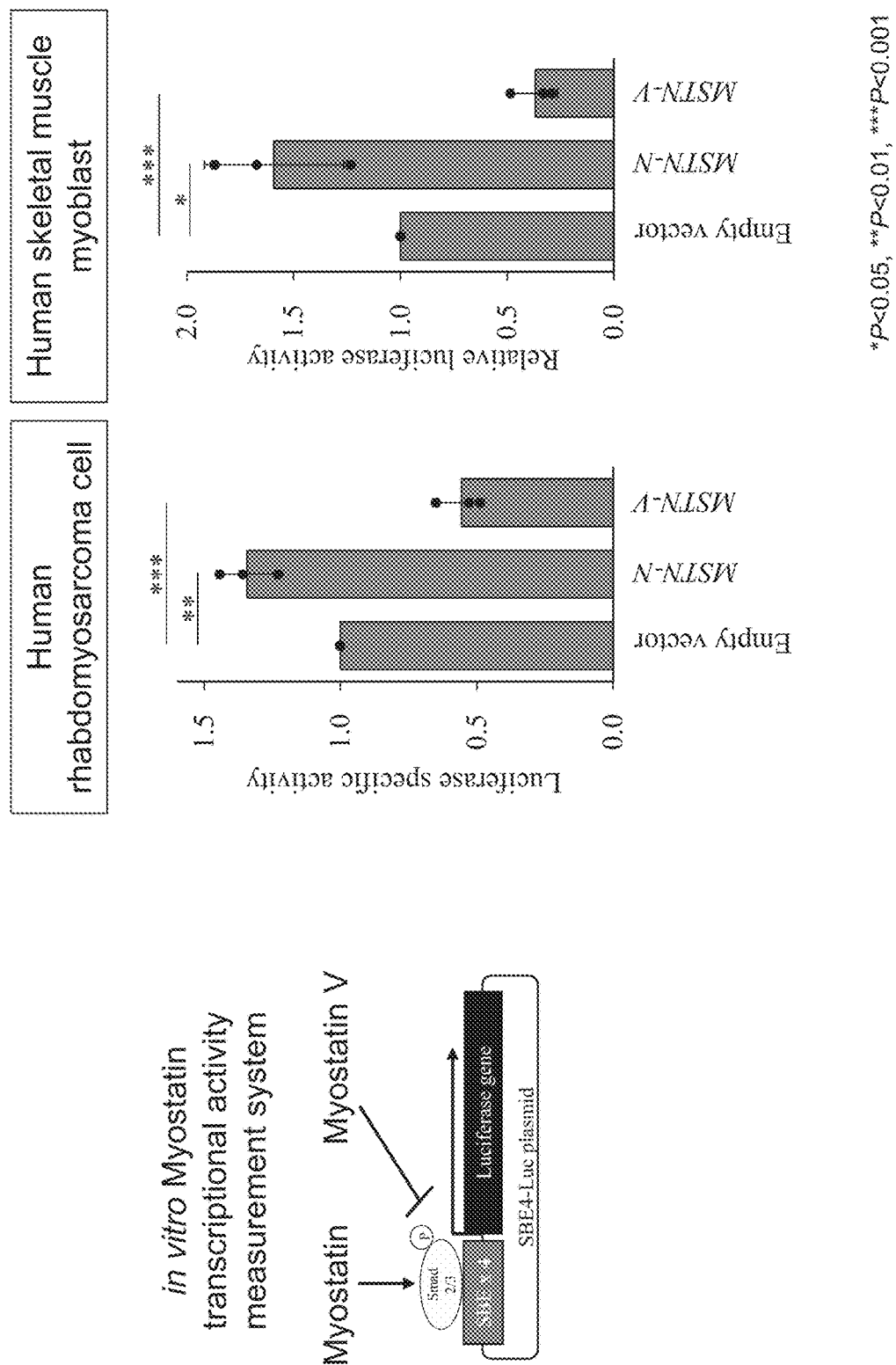

FIG. 6 Inhibition of Myostatin Signaling by Myostatin V

Effects of myostatin V and myostatin on in vitro myostatin transcriptional activity measurement system are shown schematically (left panel). Myostatin signaling was evaluated by introducing an empty vector, MSTN-N expression vector and MSTN-V expression vector individually into myocytes, and measuring the activity of luciferase whose expression is induced by Smad2/3.

Luciferase activity was shown in relative values with the result of measurement of liquid extract from empty vector-introduced cell being taken as 1 (middle and right panels). In both human rhabdomyosarcoma cell and human skeletal muscle myoblast cell, luciferase specific activity was elevated when myostatin was expressed. On the other hand, when myostatin V was expressed, decrease in luciferase specific activity was recognized, suggesting that myostatin V inhibits myostatin signal transduction.

BEST MODES FOR CARRYING OUT THE INVENTION

Hereinbelow, embodiments of the present invention will be described in detail.

The present invention provides the following protein (a) or (b):
(a) a protein comprising the amino acid sequence as shown in SEQ ID NO: 1
(b) a protein comprising an amino acid sequence having at least 70% or more sequence identity with the amino acid sequence as shown in SEQ ID NO: 1 and which yet is capable of inhibiting myostatin signaling.

The protein of (a) is a protein comprising the amino acid sequence as shown in SEQ ID NO: 1 and is a protein translated from a splice variant of human myostatin. As shown in FIG. 3, myostatin (375aa, 43 kDa) is composed of signal peptide (1-18), prodomain (19-266) and mature myostatin (267-375), whereas the myostatin variant is composed of signal peptide (1-18) and part of prodomain (19-251) with C-terminus amino acid (251) being valine instead of proline. Therefore, no mature myostatin is formed in the myostatin variant.

The protein of (a) is capable of inhibiting myostatin signaling (FIG. 4).

The protein of (a) may be prepared as described below. Briefly, RNA is extracted from human rhabdomyosarcoma cell (CRL-2061, ATCC) and cDNA is synthesized using reverse transcriptase and random primers. After PCR amplification, sequence analysis is performed for sequence determination. Then, the sequence is optimized for codon usage frequency in the open reading frame and gets a restriction enzyme recognition site to be added at 5' end and 3' end; the resultant sequence is then incorporated into an appropriate vector which is introduced into an appropriate host cell to allow production of a recombinant protein. Thus, the protein of (a) is prepared as a recombinant protein.

The protein of (b) is a protein comprising an amino acid sequence having at least 70% or more sequence identity with the amino acid sequence as shown in SEQ ID NO: 1 and which yet is capable of inhibiting myostatin signaling. As described in one Example provided later, when signal transduction is activated by myostatin, a transcription factor (Smad protein) binds to an Smad binding sequence to thereby induce transcription. Using this phenomenon, it is possible to evaluate the presence or absence of inhibition of myostatin signaling; specifically, a reporter gene in which a luciferase gene is located downstream of the Smad binding sequence and an expression vector for the protein of (b) are co-introduced into a cell and then the resultant luciferase luminescence is measured.

Sequence identity between the amino acid sequences of the protein of (a) and the protein of (b) is at least 70% or more. Further, sequence identity is more preferable in the following order: 80% or more, 90% or more, 95% or more, 98% or more. The protein of (b) may be a protein comprising the amino acid sequence as shown in SEQ ID NO: 1 wherein one or a plurality of amino acids (ranging in number from 2 to 76, preferably in the increasing order of 2, 3, 4, 5, 6, 7, 8, 9, 10, 20, 30, 40, 50, 60, 70, 75 and 76) are deleted, substituted or added and which yet is capable of inhibiting myostatin signaling.

The protein of (b) may be prepared by substituting arbitrary amino acids in the protein of (a) with other amino acids by site-directed mutagenesis.

The present invention provides a polynucleotide comprising a nucleotide sequence encoding the protein of (a) or (b) or a sequence complementary to the nucleotide sequence.

The polynucleotide of the present invention may be either single- or double-stranded. When the polynucleotide is double-stranded, it comprises a polynucleotide comprising a nucleotide sequence encoding the protein of (a) or (b) and a strand complementary thereto.

The polynucleotide may be either DNA, RNA or chimera DNA/RNA. Nucleotides constituting the polynucleotide may be modified. Examples of modified nucleotide include those nucleotides in which sugar is modified (e.g., D-ribofuranose is 2'-O-alkylated or D-ribofuranose is 2'-O, 4'-C-alkylenated), those nucleotides in which phosphodiester bond is modified (e.g., thioated), those nucleotides in which base is modified, a combination of the above-described nucleotides, and so forth.

As one example of the nucleotide sequence encoding the protein of (a), the nucleotide sequence as shown in SEQ ID NO: 2 may be given. The nucleotide sequence as shown in SEQ ID NO: 2 is an mRNA sequence for a myostatin variant extracted from human rhabdomyosarcoma cell (CRL-2061, ATCC). The nucleotide sequence as shown in SEQ ID NO: 2 contains 5' untranslated region, open reading frame (sequence between start codon (atg) and stop codon (tga)), 3' untranslated region and poly(A). The nucleotide sequence encoding the protein of (a) may be the sequence between the start codon (atg) and the stop codon (tga) in the nucleotide sequence of SEQ ID NO: 2, or a nucleotide sequence comprising the sequence between the start codon and the stop codon. The nucleotide sequence in the open reading frame may be optimized for codon usage frequency. As one example of such optimization, a nucleotide sequence optimized for codon usage frequency in the open reading frame of SEQ ID NO. 2 is shown in SEQ ID NO: 3.

A polynucleotide comprising a nucleotide sequence encoding the protein of (a) may be prepared, for example, by the method disclosed in Example 1 described later.

A polynucleotide comprising a sequence complementary to a nucleotide sequence encoding the protein of (a) may be synthesized from mRNA (having poly(A) chain at 3' end) of a myostatin variant comprising the nucleotide sequence encoding the protein of (a) using reverse transcriptase and oligo dT primers. After degrading mRNA by alkali treatment, the resultant single-stranded DNA may be used as a template for conversion into a double-stranded DNA using reverse transcriptase or DNA polymerase.

A nucleotide sequence encoding the protein of (b) and a sequence complementary thereto may be obtained, for example, by introducing base substitution mutations into a nucleotide sequence encoding the protein of (a) and a sequence complementary thereto by site-directed mutagenesis.

To prepare the protein of (a) or (b), a DNA encoding the protein of (a) or (b) may be incorporated into a vector to thereby prepare a recombinant vector, which is then introduced into a host cell to thereby transform the cell; the transformed cell is cultured to produce the protein of (a) or (b). Therefore, the present invention provides a method of preparing the protein of (a) or (b), which comprises culturing a cell comprising a vector comprising a polynucleotide comprising a nucleotide sequence encoding the protein of (a) or (b) or a sequence complementary thereto. The present invention also provides a vector (recombinant vector) comprising a polynucleotide comprising a nucleotide sequence encoding the protein of (a) or (b) or a sequence complementary thereto. Moreover, the present invention provides a cell comprising a vector comprising a polynucleotide comprising a nucleotide sequence encoding the protein of (a) or (b) or a sequence complementary thereto.

The recombinant vector of the present invention may be obtained by inserting a polynucleotide comprising a nucleotide sequence encoding the protein of (a) or (b) and a sequence complementary thereto into an appropriate vector.

As the vector, Escherichia coli-derived plasmids (e.g., pBR322, pBR325, pUC12, pUC13, pUC19, pET-44 or pBlueScriptII); Bacillus subtilis-derived plasmids (e.g., YEp13, pYES2, YRp7, YIp5, pYAC2, pUB110, pTP5 or pC194), yeast-derived plasmids (e.g., pSH19 or pSH15); bacteriophages such as λ phage; animal viruses such as retrovirus, adenovirus, lentivirus, adeno-associated virus or vaccinia virus; or insect pathogen viruses such as baculovirus may be used.

The expression vector may also comprise promoters, enhancers, terminators, splicing signals, poly-A addition signals, selection markers, SV40 replication origins, and so forth.

Further, the expression vector may be a fusion protein expression vector. Various types of fusion protein expression vectors are commercially available, as exemplified by pGEX series (GE Healthcare), Novagen™ pET Systems (Merck), Clontech fluorescent protein vector series (Takara), His6 HaloTag™ vector for expression of tag-added protein (Promega), FLAG-tagged fusion protein expression system (Sigma-Aldrich), pCruz™ expression vector series for mammalian cells (Santa Cruz Biotechnology) and so forth.

It is possible to obtain a transformant by introducing the recombinant vector of the present invention into a host cell. The present invention also provides a recombinant vector-introduced cell (host cell).

Examples of the host cell include, but are not limited to, bacterial cells (such as Escherichia bacteria, Bacillus bacteria or Bacillus subtilis), fungal cells (such as yeast or Aspergillus), insect cells (such as S2 cells or Sf cells), animal cells (such as CHO cells, COS cells, HeLa cells, C127 cells, 3T3 cells, BHK cells or HEK 293 cells) and plant cells.

Introduction of a recombinant vector into a host cell may be performed by the methods disclosed in Molecular Cloning 2nd Edition, J. Sambrook et al., Cold Spring Harbor Lab. Press, 1989 (e.g., the calcium phosphate method, the DEAE-dextran method, transfection, microinjection, lipofection, electroporation, transduction, scrape loading, the shotgun method, etc.) or by infection.

The transformant may be cultured in a medium, followed by collection of the protein of (a) or (b) from the culture. In the case where the protein of (a) or (b) is secreted into the medium, the medium may be recovered, followed by isolation and purification of the protein of (a) or (b) from the medium. In the case where the protein of (a) or (b) is produced within the transformed cells, the cells may be lysed, followed by isolation and purification of the protein from the cell lysate.

In the case where the protein of (a) or (b) is expressed in the form of a fusion protein fused to another protein (functioning as a tag), the fusion protein is isolated and purified before treatment with factor Xa or an enzyme (enterokinase) is performed to cut off another protein, whereby the protein of (a) or (b) is obtained.

Isolation and purification of the protein of (a) or (b) may be performed by known methods. Known isolation/purification methods which may be used in the present invention include, but are not limited to, methods using difference in solubility (such as salting-out or solvent precipitation); methods using difference in molecular weight (such as dialysis, ultrafiltration, gel filtration or SDS-polyacrylamide gel electrophoresis); methods using difference in electric charge (such as ion exchange chromatography); methods using specific affinity (such as affinity chromatography); methods using difference in hydrophobicity (such as reversed phase high performance liquid chromatography); and methods using difference in isoelectric point (such as isoelectric focusing).

It is possible to promote myogenesis by inhibiting myostatin signaling using the protein of the present invention, a polynucleotide comprising a nucleotide sequence encoding the protein of the present invention or a sequence complementary thereto, a vector comprising the polynucleotide or a cell comprising the vector. Therefore, the present invention provides a composition for inhibiting myostatin signaling, comprising at least one member selected from the group consisting of the protein of (a) and/or (b), a polynucleotide comprising a nucleotide sequence encoding the protein or a sequence complementary thereto, a vector comprising the polynucleotide, and a cell comprising the vector. Further, the present invention provides a composition for promoting myogenesis, comprising at least one member selected from the group consisting of the protein of (a) and/or (b), a polynucleotide comprising a nucleotide sequence encoding the protein or a sequence complementary to the nucleotide sequence, a vector comprising the polynucleotide, and a cell comprising the vector. In the case where a polynucleotide comprising a nucleotide sequence encoding the protein of (a) and/or (b) or a sequence complementary thereto is to be incorporated into a vector, the vector may be such that the polynucleotide comprising a nucleotide sequence encoding the protein of (a) and/or (b) or a sequence complementary thereto can be introduced into cells. Examples of such vector include, but are not limited to, vectors for gene therapy such as adenovirus, retrovirus, lentivirus, adeno-associated virus, Sendai virus, liposome and plasmids. Moreover, those cells (autologous or allogeneic) into which the polynucleotide or vector of the present invention has been introduced may be used in cell therapy. Methods of introducing a gene of interest into a vector, methods of introducing a recombinant vector into a cell, methods of administering a recombinant vector or a transgenic cell to human or the sites of administration are known. These methods, either as such or with necessary modifications, may be applicable to the present invention. In gene therapy or cell therapy, genome editing techniques may be used. In genome editing, artificial nucleases such as ZFN (zinc-finger nuclease), TALEN (transcription activator-like effector nuclease), CRISPR/Cas9 (clustered regularly interspaced short palindromic repeats/CRISPR-associated protein 9), or the like may be employed.

The composition of the present invention may be used in pharmaceutical drugs, experimental reagents, foods, feeds, and so on.

Such pharmaceutical drugs may be used for preventing and/or treating diseases in which myostatin is involved (myostatin may be involved either directly or indirectly). Specific examples of such diseases include, but are not limited to, amyotrophic diseases such as muscular dystrophy, spinal muscular atrophy, sarcopenia or disuse muscle atrophy; cardiovascular diseases such as heart failure or arteriosclerosis; renal diseases such as chronic renal failure; bone diseases such as inflammatory arthritis; cancer or diabetes. Diseases in which myostatin is involved may advantageously be those diseases which can be effectively coped by decrease in myostatin level or inhibition of myostatin signaling. The present invention provides a method for preventing and/or treating a disease in which myostatin is involved, comprising administering to a subject a pharmaceutically effective amount of at least one member selected from the group consisting of the protein of (a) and/or (b), a polynucleotide comprising a nucleotide sequence encoding the protein or a sequence complementary thereto, a vector comprising the polynucleotide, and a cell comprising the vector. Further, the present invention provides at least one member selected from the group consisting of the protein of (a) and/or (b), a polynucleotide comprising a nucleotide sequence encoding the protein or a sequence complementary thereto, a vector comprising the polynucleotide, and a cell comprising the vector for use in a method of preventing and/or treating a disease in which myostatin is involved.

Myostatin inhibition leads to an increase in skeletal muscle mass and, hence, can be used for treatment of all diseases that present with muscular atrophy whatever etiology it has. Increase in skeletal muscle mass contributes to an increased amount of exercise and an improvement of systemic metabolism as well. Further, increased skeletal muscle mass is expected to affect cardiac muscle in a favorable way to restore its function.

Myostatin inhibition is also expected to have other effects such as acting on osteoclast cells to inhibit osteoclast, activating the homeostatic capacity of vascular endothelial cells, inducing apoptosis, and increasing insulin sensitivity.

At least one member selected from the group consisting of the protein of (a) and/or (b), a polynucleotide comprising a nucleotide sequence encoding the protein or a sequence complementary thereto, a vector comprising the polynucleotide, and a cell comprising the vector (hereinafter, referred to as "active ingredient") may be administered either alone or together with pharmacologically acceptable carriers, diluents or excipients in appropriate forms of pharmaceutical compositions, to mammals (e.g., human, rabbit, dog, cat, rat, mouse, etc.) orally or parenterally. Dose levels may vary depending on the subject to be treated, the target disease, symptoms, administration route, and so on. For example, in the case of use for prevention/treatment of an amyotrophic disease (e.g., muscular dystrophy), the amounts indicated below may be administered as a dose per administration in terms of active ingredient. When the active ingredient is a protein, usually approx. 0.1 μg to 100 mg/kg body weight, preferably approx. 0.5 mg to 100 mg/kg body weight; when the active ingredient is a polynucleotide, usually approx. 0.1 to 50 mg/kg body weight, preferably approx. 0.5 mg/kg body weight; and when the active ingredient is a vector comprising the polynucleotide, usually approx. $1 \times 10^{14}$ to $9 \times 10^{14}$ genome copies/kg body weight, preferably approx. $1 \times 10^{12}$ genome copies/kg body weight, may be administered at a frequency of about once a week to once a month or once a year, preferably at a frequency of about once a year, either orally or by intramuscular, subcutaneous, or intravenous injection (preferably, consecutive or alternate day administration). When the active ingredient is a cell comprising the vector, 10,000 to 100,000 cells may be administered as a dose per administration in terms of active ingredient, at a frequency of about once a week to once a month or once a year, preferably at a frequency of about once a year, by intramuscular, subcutaneous or intravenous injection, preferably by intravenous injection.

In cases of other parenteral administration and oral administration, similar dose levels may be used. If symptoms are particularly severe, the dose may be increased accordingly.

Compositions for oral administration include solid or liquid preparations such as tablets (including sugar-coated tablets and film-coated tablets), pills, granules, powders, capsules (including soft capsules), syrups, emulsions and suspensions. These compositions may be prepared according to conventional methods and may contain carriers, diluents or excipients conventionally used in the field of medicine manufacture. For example, lactose, starch, sucrose, magnesium stearate and the like are used as carriers or excipients for tablets.

Compositions for parenteral administration include, for example, injections and suppositories. Injections include intravenous injections, subcutaneous injections, intradermal injections, muscle injections, instilment injections, etc. Such injections may be prepared by conventional methods, i.e., by dissolving, suspending or emulsifying the active ingredient in an aseptic, aqueous or oily liquid conventionally used in injections. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80, HCO-50 (polyoxyethylene (50 mol) adduct of hydrogenated castor oil)], etc. Examples of oily liquids for injection include sesame oil and soybean oil. They may be used in combination with an auxiliary solubilizer such as benzyl benzoate, benzyl alcohol, etc. Usually, the prepared injections are filled in appropriate ampoules. Suppositories for administration into the rectum may be prepared by mixing the active ingredient with a conventional suppository base.

The above-described pharmaceutical compositions for oral or parenteral administration may be formulated into unit dosage forms that would give an appropriate dose of the active ingredient. Examples of such unit dosage forms include tablets, pills, capsules, injections (ampoules), and suppositories. Preferably, 0.1 to 1000 mg of the active ingredient is usually contained in each unit dosage form.

As regards foods and feeds, they may be used for promoting myogenesis in human and other animals. Animals may be those which are expressing myostatin. Domestic animals used for work, food or pet, or fishes under culture, specifically mammals such as cat, dog, sheep, pig or cattle; poultry such as chicken or turkey; fishes such as salmon, trout, cod fish, tuna or yellowtail may be enumerated.

The following may be added to the food or feed of the present invention: general ingredients such as protein, fat, carbohydrate, and sodium; minerals such as potassium, calcium, magnesium, and phosphorus; trace elements such as iron, zinc, copper, selenium, and chromium; vitamins such as vitamin A, β-carotene, vitamin B1, vitamin B2, vitamin B6, vitamin B12, vitamin C, niacin, folic acid, vitamin D3, vitamin E, biotin, and pantothenic acid; and other substances such as coenzyme Q10, α-lipoic acid, galacto-oligosaccharide, dietary fiber, an excipient (such as water, carboxymethyl cellulose, or lactose), a sweetener, a flavoring agent (such as malic acid, citric acid, or amino acid), and a fragrance. When the food or feed of the present invention is provided as a liquid food or feed, water, physiological saline, soup, milk, fruit juice, or the like can be used as a liquid in which the food or feed ingredients are dispersed or dissolved. The food or feed of the present invention may be formulated into such forms as powder, granules, tablets or liquid preparations. In order to help patients or elderly persons have easy access to its intake, the food of the invention is preferably in the form of a gel-like (gelatinous?) product such as jelly.

The food or feed of the present invention may be ingested in such an amount, frequency and period of intake that the desired effect can be confirmed.

EXAMPLES

Hereinbelow, the present invention will be described in detail with reference to the following Examples. However, the present invention is not limited to these Examples.

[Example 1] Cloning and Identification of Myostatin Variant

Figure 1:
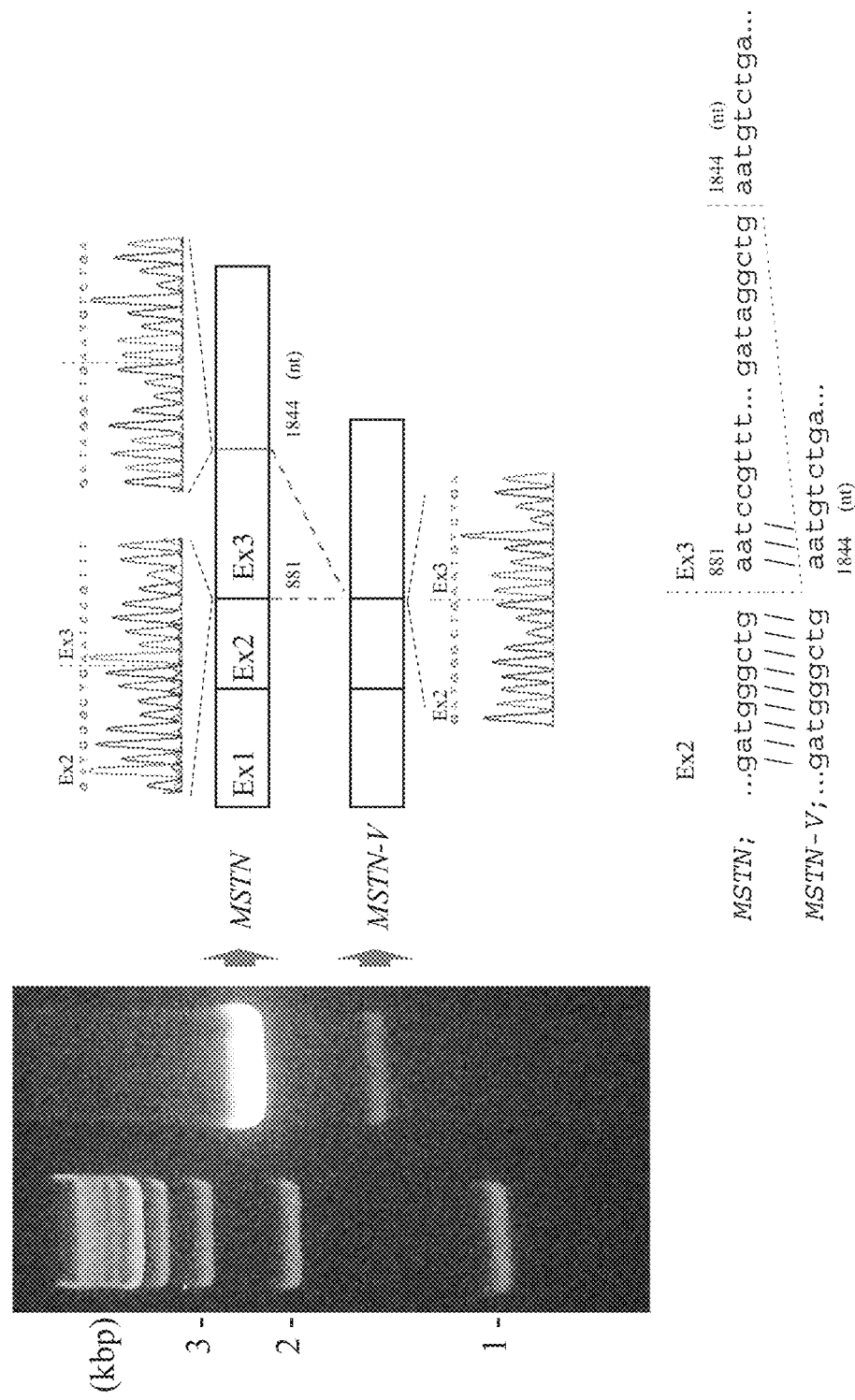
FIG. 1 Example of PCR Amplification of Myostatin V

RNA (500 ng) extracted from human rhabdomyosarcoma cell (CRL-2061, ATCC) using High Pure RNA Isolation Kit (#11828665001, Roche Life Science) was reverse-transcribed to cDNA by M-MLV Reverse Transcriptase (#28025013, Thermo Fisher Scientific) using Random primers (#48190011, Thermo Fisher Scientific) in the presence of RNaseOUT™ Recombinant Ribonuclease Inhibitor (#10777-019, Thermo Fisher Scientific). The resultant cDNA was subjected to PCR using primers MSTN Ex1_F1; 5'-agattcactggtgtggcaag-3' (SEQ ID NO: 6) and MSTN R2; 5'-tgcatgacatgtctttgtgc-3' (SEQ ID NO: 7) and TaKaRa Ex Taq™ DNA polymerase (#RR001A, Takara). PCR products were electrophoresed on agarose gel. Upon electrophoresis, two amplified bands were detected between 2 kbp and 3 kbp and between 1 kbp and 2 kbp of DNA size markers, respectively. Two PCR fragments of 2.5 kbp and 1.5 kbp were obtained from these bands (FIG. 1, left panel). DNA was extracted from each fragment with MinElute™ Gel Extraction Kit (#28604, Qiagen), and the extracted DNA fragment was subcloned into pT7Blue (#69820, Novagen) with DNA Ligation Kit Ver. 2.1 (#6022, Takara). The subcloned sequence was amplified by PCR using primers MSTN Ex1_F1 and MSTN R2 and TaKaRa Ex Taq™ DNA polymerase (#RR001A, Takara). After purification with MinElute™ PCR Purification Kit (#28006, QIAGEN), sequence analysis was performed by the Sanger method.

The results of sequencing revealed that the PCR fragment of approx. 2.5 kbp is a normal splicing product (MSTN) composed of all the exons of myostatin (MSTN) gene: exon 1 (Ex1), exon 2 (Ex2) and exon 3 (Ex3). A schematic drawing of this MSTN is shown in FIG. 1, right panel. Part of the sequence of the junction site between exon 2 and exon 3, and part of the nucleotide sequence starting from nucleotide No. 1844 in exon 3 are shown in FIG. 1, right lower panel. The nucleotide sequence of the PCR fragment of approx. 1.5 kbp (which is a myostatin variant MSTN-V) (SEQ ID NO: 2) was completely identical with the nucleotide sequence of MSTN as far as exon 1 and exon 2 of myostatin gene are concerned. However, the sequence of MSTN-V corresponding to exon 3 was completely different from that of MSTN. The sequence starting with "aat ccg ttt" was changed to a sequence starting with "aat gtc tga". The sequence starting with this "aat gtc tga" was completely identical with the sequence downstream from nucleotide No. 1844 in exon 3 of MSTN. This indicated that a region corresponding to the region spanning from nucleotide No. 881 to No. 1843 in exon 3 of MSTN was missing in MSTN-V.

Intron 2 of MSTN is the most common intron having GT sequence and AG sequence at 5' end and 3' end, respectively. On the other hand, the mode of splicing of intron 2 is different in MSTN-V; TG in exon 3 (which is a cryptic splice acceptor site) is activated to thereby form a GT-TG intron. As a result, 963 nucleotides spanning from nucleotide No. 881 to No. 1843 in exon 3 are deleted in MSTN-V (FIG. 2).

The identified MSTN-V mRNA has start codon and stop codon, and it was suggested that this mRNA is translated to a protein of 251 amino acids. Up to the 250th amino acid from N terminus of myostatin V, the sequence of myostatin V was the same as that of myostatin, but the $251^{st}$ amino acid was valine (V) and the $252^{nd}$ position was stop codon. Since mature myostatin is composed of amino acids from No. 267 to No. 375 of myostatin, mature myostatin is not produced from MSTN-V mRNA (SEQ ID NO: 1, FIG. 3).

Myostatin exerts its effect via myostatin signaling. Briefly, when mature myostatin generated from precursor binds to its receptor present in the cell membrane, Smad2/3 is phosphorylated. The phosphorylated Smad2/3 transits into the nucleus and binds to Smad binding element located upstream of a target gene to thereby enhance expression of the target gene (FIG. 4). The amino acid sequence of myostatin precursor is shown in SEQ ID NO: 5 and the sequence of mRNA in SEQ ID NO: 4.

[Example 2] Expression of Myostatin Variant in Cultured Cells

For expressing myostatin V in cultured cells, MSTN-V expression vector was prepared. Briefly, codon usage frequency in the open reading frame of SEQ ID NO: 2 was optimized to thereby obtain SEQ ID NO: 3. A nucleic acid sequence having Nhe I recognition sequence (GCTTGC) and BamH I recognition sequence (GGATCC) added to 5' and 3' end of SEQ ID NO: 3, respectively, was artificially synthesized in Fasmac Co., and inserted into the Nhe I/BamH I recognition site of pcDNA™3.1 (+) vector (#V79020, Thermo Fisher Scientific) (FIG. 5, left panel).

Protein expression from the MSTN-V expression vector was confirmed by Western blotting. The MSTN-V expression vector and an empty vector for control (pcDNA™M3.1 (+)) were introduced into human rhabdomyosarcoma cell (CRL-2061, ATCC) using Lipofectamin™ 2000 (#11668019, Thermo Fisher Scientific). Twenty-four hours after introduction of the vectors, cells were disrupted using Cell Lysis Buffer (#9803, Cell Signaling) (supplemented with 1 mM PMSF (#8553, Cell Signaling)) to obtain soluble fractions as a sample. Quantification of the protein in the thus obtained sample was performed using Qubit™ Protein Assay Kit (#Q33211, Thermo Fisher Scientific). Sample for SDS-PAGE was prepared by mixing the above-mentioned sample with 4× Laemmli Sample Buffer (#1610747, Bio-Rad) (supplemented with 2-Mercaptoethanol (#1610710, Bio-Rad)) and thermally treating the resultant mixture. SDS-PAGE was performed with Mini-PROTEAN™ TGX™ Precast Gels 4-20% Gel (#456-1094, BIO-RAD). As molecular marker, Precision Plus Protein™ Dual Color Standards (#1610374, BIO-RAD) were electrophoresed. For transfer onto membrane, TransBlot Turbo™ transcription system (Bio-Rad) was used. Protein-transferred membrane was blocked with 2% ECL™ Prime Blocking Agent (#RPN418, Amersham) at room temperature for 1 hour. Then, the membrane was treated with a primary antibody recognizing either the N-terminal side of myostatin (Anti-GDF8/Myostatin antibody, #ab71808, abcam) or actin (β-Actin antibody (C4), #sc-47778, Santa Cruz Biotechnology) at 4° C. overnight. As secondary antibody, HRP-labeled anti-rabbit IgG antibody (#NA934, GE) or HRP-labeled anti-mouse IgG antibody (#NA931, GE) was used. The membrane was treated at room temperature for 1 hour. Detection was performed with Amersham™ ECL Select™ Western Blotting Detection Reagent (#RPN2235, GE) using ChemiDoc™ XRS+ system (Bio-Rad). As a result, a band of myostatin V was detected at around 35 kDa (FIG. 5, right panel). At the same time, actin was also analyzed to obtain a band.

[Example 3] Inhibition of Myostatin Signaling by Myostatin Variant

Myostatin signaling inhibitory activity by myostatin V was evaluated using in vitro myostatin transcriptional activity measurement system. In this evaluation system, a reporter gene (SBE4-Luc plasmid, #16495, Addgene) having a luciferase gene located downstream of an Smad binding sequence was introduced into cells. Then, luminescence of luciferase induced for expression was measured, whereby myostatin signaling was evaluated (FIG. 6, left panel). In addition to MSTN-V expression vector, myostatin (MSTN-N) expression vector was also used for the purpose of examination. MSTN-N expression vector was prepared as described below. Briefly, a nucleic acid sequence having Nhe I recognition sequence (GCTTGC) and BamH I recognition sequence (GGATCC) added to 5' and 3' end of myostatin cDNA (SEQ ID NO: 4), respectively, was artificially synthesized in Fasmac Co. and inserted into the Nhe I/BamH I recognition site of pcDNA™3.1 (+) vector (#V79020, Thermo Fisher Scientific). Expression of myostatin (SEQ ID NO: 5) from MSTN-N expression vector was confirmed by Western blotting in the same manner as described for myostatin V.

Two types of vectors were co-introduced into human rhabdomyosarcoma cell (CRL-2061, ATCC) and human skeletal muscle myoblast cell using Lipofectamin™ 2000 (#11668019, Thermo Fisher Scientific). One of the two vector types was SBE4-Luc plasmid and the other type was MSTN-V expression vector or MSTN-N expression vector or empty vector (pcDNA™3.1 (+)). Twenty-four hours after the vector introduction, cells were disrupted using the Reporter Lysis Buffer of Luciferase Assay System with Reporter Lysis Buffer (#E4030, Promega) to obtain soluble fractions as a sample. Quantification of the protein in the thus obtained sample was performed using Qubit™ Protein Assay Kit (#Q33211, Thermo Fisher Scientific). Luciferase activity was evaluated by measuring luciferase luminescence signals on multi-label plate reader ARVO™3 (PerkinElmer) using the Luciferase Assay System of Luciferase Assay System with Reporter Lysis Buffer (#E4030, Promega) as a substrate.

Luciferase activity was shown in terms of relative values with the result of measurement of a liquid extract from empty vector-introduced cell taken as 1 (FIG. 6, middle and right panels). In both human rhabdomyosarcoma cells and human skeletal muscle myoblast cells, luciferase specific activity was shown to increase when myostatin was expressed. On the other hand, when myostatin V was expressed, a decrease in luciferase specific activity was recognized. Luciferase activity measured in this experimental system correlates with myostatin signaling. The increase in luciferase activity shows enhancement of myostatin signaling, and the decrease in luciferase activity shows inhibition of luciferase signaling. From these results, it has become clear that myostatin signaling is inhibited by expression of myostatin V.

All publications, patents and patent applications cited herein are incorporated herein by reference in their entirety.

INDUSTRIAL APPLICABILITY

The present invention is applicable to promotion of myogenesis in human and animals.

---

[SEQUENCE LISTING FREE TEXT]

<SEQ ID NO: 1>
The amino acid sequence of a myostatin variant protein is shown (a total of 251 amino acids).

```
1   MQKLQLCVYIYLFMLIVAGPVDLNENSEQKENVEKEGLCNACTWRQNTKSSRIEATKIQI      60

LSKLRLETAPNISKDVIRQLLPKAPPLRELIDQYDVQRDDSSDGSLEDDDYHATTETIIT     120

MPTESDFLMQVDGKPKCCFFKFSSKIQYNKVVKAQLWIYLRPVETPTTVFVQILRLIKPM     180

KDGTRYTGIRSLKLDMNPGTGIWQSIDVKTVLQNWLKQPESNLGIEIKALDENGHDLAVT     240

FPGPGEDGLNV                                                      251
```

<SEQ ID NO: 2>
The nucleotide sequence of a myostatin variant is shown (a total of 1860 nucleotides; start codon (atg) and stop codon (tga) are individually indicated in a rectangle).

```
agattcactggtgtggcaagttgtctctcagactgtacatgcattaaaattttgcttggc      60 attactcaaaagcaaagaaaagtaaaaggaagaaacaagaacaagaaaaaagattatat    120 tgattttaaaatc atg caaaaactgcaactctgtgtttatatttacctgtttatgctgat   180 tgttgctggtccagtggatctaaatgagaacagtgagcaaaaagaaaatgtggaaaaga    240 ggggctgtgtaatgcatgtacttggagacaaaacactaaatcttcaagaatagaagccat   300 taagatacaaatcctcagtaaacttcgtctggaaacagctcctaacatcagcaaagatgt   360 tataagacaacttttacccaaagctcctccactccgggaactgattgatcagtatgatgt   420
```

| | |
|---|---|
| ccagagggatgacagcagcgatggctctttggaagatgacgattatcacgctacaacgga | 480 |
| aacaatcattaccatgcctacagagtctgattttctaatgcaagtggatggaaaacccaa | 540 |
| atgttgcttctttaaatttagctctaaaatacaatacaataaagtagtaaaggcccaact | 600 |
| atggatatatttgagacccgtcgagactcctacaacagtgtttgtgcaaatcctgagact | 660 |
| catcaaacctatgaaagacggtacaaggtatactggaatccgatctctgaaacttgacat | 720 |
| gaacccaggcactggtatttggcagagcattgatgtgaagacagtgttgcaaaattggct | 780 |
| caaacaacctgaatccaacttaggcattgaaataaaagctttagatgagaatggtcatga | 840 |
| tcttgctgtaaccttcccaggaccaggagaagatgggctgaatgtctgaggctaccaggt | 900 |
| ttatcacataaaaaacattcagtaaaatagtaagtttctcttttcttcaggtgcattttc | 960 |
| ctacacctccaaatgaggaatggattttctttaatgtaagaagaatcattttctagagg | 1020 |
| ttggctttcaattctgtagcatacttggagaaactgcattatcttaaaaggcagtcaaat | 1080 |
| ggtgtttgttttatcaaaatgtcaaaataacatacttggagaagtatgtaattttgtct | 1140 |
| ttggaaaattacaacactgcctttgcaacactgcagtttttatggtaaaataatagaaat | 1200 |
| gatcgactctatcaatattgtataaaaagactgaaacaatgcatttatataatatgtata | 1260 |
| caatattgttttgtaaataagtgtctccttttttatttactttggtatattttttacacta | 1320 |
| aggacatttcaaattaagtactaaggcacaaagacatgtcatgcatcacagaaaagcaac | 1380 |
| tacttatatttcagagcaaattagcagattaaatagtggtcttaaaactccatatgttaa | 1440 |
| tgattagatggtttatattacaatcattttatattttttacatgattaacattcacttat | 1500 |
| ggattcatgatggctgtataaagtgaatttgaaatttcaatggtttactgtcattgtgtt | 1560 |
| taaatctcaacgttccattatttaatacttgcaaaaacattactaagtataccaaaata | 1620 |
| attgactctattatctgaaatgaagaataaactgatgctatctcaacaataactgttact | 1680 |
| tttattttataatttgataatgaatatatttctgcatttatttacttctgttttgtaaat | 1740 |
| tgggattttgttaatcaaatttattgtactatgactaaatgaaattatttcttacatcta | 1800 |
| atttgtagaaacagtataagttatattaaagtgttttcacatttttttgaaagacaaaaa | 1860 |

<SEQ ID NO: 3>
The nucleotide sequence of myostatin V (MSTN-V) incorporated into an expression vector. Before insertion into the vector, Nhe I site was added to 5' side and BamH I site to 3' side. (a total of 1860 nucleotides; start codon (atg) and stop codon (tga) are individually indicated in a rectangle).

| | |
|---|---|
| agattcactggtgtggcaagttgtctctcagactgtacatgcattaaaattttgcttggc | 60 |
| attactcaaaagcaaaagaaaagtaaaaggaagaaacaagaacaagaaaaaagattatat | 120 |
| tgatttaaaatcatgcagaagctccagctttgcgtgtacatctacctgttcatgctgat | 180 |
| agttgcaggcccagtggatctgaatgagaacagcgaacagaaggagaacgtagagaagga | 240 |
| aggcttgtgcaatgcctgtacttggcggcagaatacgaaatcttcccgtattgaggccat | 300 |
| caagatccagattctcagcaaactgcgccttgaaactgcacctaacatcagcaaggacgt | 360 |
| aatcagacagcttctgcccaaagctcctccactgagagagctcattgaccagtacgacgt | 420 |
| ccaacgagatgacagttcagatggctcacttgaggatgacgactatcatgccactaccga | 480 |
| aaccatcattacaatgccgaccgaaagcgatttcctgatgcaagtggatgggaaaccaaa | 540 |
| gtgttgcttcttcaagttttcctccaagatccagtacaacaaagtcgtcaaggcgcaact | 600 |
| gtggatatatctgagcccgttgagactccaacaaccgtgtttgtgcagattttgaggct | 660 |
| gatcaagcccatgaaagacggaacacgctataccggaatacggagtctgaaactggacat | 720 |

-continued

| | |
|---|---|
| gaatcccggtacagggatttggcagtctatcgacgtcaaaacggttctccagaactggct | 780 |
| gaaacaaccggagtctaatctcgggattgagatcaaggccttggacgaaaatggccacga | 840 |
| tctggctgtgacctttcctggtcctggagaagatggcctgaacgtc tga ggctaccagt | 900 |
| ttatcacataaaaaacattcagtaaaatagtaagtttctcttttcttcaggtgcattttc | 960 |
| ctacacctccaaatgaggaatggattttctttaatgtaagaagaatcattttttctagagg | 1020 |
| ttggctttcaattctgtagcatacttggagaaactgcattatcttaaaaggcagtcaaat | 1080 |
| ggtgtttgttttatcaaaatgtcaaaataacatacttggagaagtatgtaattttgtct | 1140 |
| ttggaaaattacaacactgcctttgcaacactgcagtttttatggtaaaataatagaaat | 1200 |
| gatcgactctatcaatattgtataaaaagactgaaacaatgcatttatataatatgtata | 1260 |
| caatattgttttgtaaataagtgtctccttttttatttactttggtatattttttacacta | 1320 |
| aggacatttcaaattaagtactaaggcacaaagacatgtcatgcatcacagaaaagcaac | 1380 |
| tactatatttcagagcaaattagcagattaaatagtggtcttaaaactccatatgttaa | 1440 |
| tgattagatggttatattacaatcattttatatttttttacatgattaacattcacttat | 1500 |
| ggattcatgatggctgtataaagtgaatttgaaatttcaatggtttactgtcattgtgtt | 1560 |
| taaatctcaacgttccattattttaatacttgcaaaaacattactaagtataccaaaata | 1620 |
| attgactctattatctgaaatgaagaataaactgatgctatctcaacaataactgttact | 1680 |
| tttattttataaatttgataatgaatatatttctgcatttatttacttctgttttgtaaat | 1740 |
| tgggattttgttaatcaaatttattgtactatgactaaatgaaattatttcttacatcta | 1800 |
| atttgtagaaacagtataagttatattaaagtgttttcacatttttttgaaagacaaaaa | 1860 |

<SEQ ID NO: 4>
The nucleotide sequence of myostatin (MSTN-N) incorporated into an expression vector. Before insertion into the vector, Nhe I site was added to 5' side and BamH I site to 3' side. (a total of 2823 nucleotides; start codon (atg) and stop codon (tga) are individually indicated in a rectangle).

| | |
|---|---|
| agattcactggtgtggcaagttgtctctcagactgtacatgcattaaaattttgcttggc | 60 |
| attactcaaaagcaaaagaaaagtaaaaggaagaaacaagaacaagaaaaaagattatat | 120 |
| tgattttaaaatc atg caaaagttgcagctgtgtgtgtacatctacctgttcatgctgat | 180 |
| tgtcgccggtcctgttgatctgaacgagaactctgagcagaaggagaacgtggagaaaga | 240 |
| aggcctgtgcaatgcttgcacatggagacagaataccaagagtagccggatagaagccat | 300 |
| tdagatccagatactgagcaagctccgcttggagacagcccctaacatttccaaggatgt | 360 |
| gatacggcaacttctgccaaaggcaccaccacttagggaactcatcgaccagtacgacgt | 420 |
| tcagagggacgatagctccgatggctctctcgaggacgatgattaccacgctactaccga | 480 |
| gactatcattacaatgcctactgagagcgactttctgatgcaagtagacgggaaacccaa | 540 |
| gtgctgcttcttcaaattctcctccaagattcagtacaataaggtcgtgaaagcccaact | 600 |
| ctggatctatctccgtccggtggaaactcctacgaccgtattcgtccagattcttaggct | 660 |
| gattaagcccatgaaagatggaacgcggtataccggcatcagaagtttgaaactggacat | 720 |
| gaatccaggtaccggaatctggcagagtatcgacgtcaaaactgtgctgcagaattggct | 780 |
| gaaacagcctgagtcaaacctggggatcgagataaaagcgctggatgaaaatgggcatga | 840 |
| tctggctgtcacctttccgggtcctggcgaagatggcctgaatcccttcctggaagtgaa | 900 |
| agtgaccgacacacccaaacgatccagaagggactttggcttggattgcgacgaacactc | 960 |
| aaccgagtctcgctgttgccgctatcctctcactgttgactttgaggcctttggatggga | 1020 |

| [SEQUENCE LISTING FREE TEXT] | |
|---|---|
| ttggatcattgctcccaagcggtacaaagcgaactactgttcaggggaatgcgagtttgt | 1080 |
| gttcctccagaagtatccgcatacacaccttgttcatcaagccaatccaagagggtctgc | 1140 |
| aggaccctgttgtacacccacgaagatgagccccatcaacatgctgtatttcaacggaaa | 1200 |
| ggaacagataatctatggcaagattccagcaatggtggtagaccgatgtggttgcagctg | 1260 |
| agatttatattaagcgttcataacttcctaaaacatggaaggttttcccctcaacaattt | 1320 |
| tgaagctgtgaaattaagtaccacaggctataggcctagagtatgctacagtcacttaag | 1380 |
| cataagctacagtatgtaaactaaaaggggggaatatgcaatggttggcatttaaccat | 1440 |
| ccaaacadatcatacaagadagttttatgatttccagagttttttgagctagaaggagatc | 1500 |
| aaattacatttatgttcctatatattacaacatcggcgaggaaatgaaagcgattctcct | 1560 |
| tgagttctgatgaattaaaggagtatgctttaaagtctatttctttaaagttttgtttaa | 1620 |
| tatttacagaaaaatccacatacagtattggtaaaatgcaggattgttatataccatcat | 1680 |
| tcgaatcatccttaaacacttgaatttatattgtatggtagtatacttggtaagataaaa | 1740 |
| ttccacaaaaatagggatggtgcagcatatgcaatttccattcctattataattgacaca | 1800 |
| gtacattaacaatccatgccaacggtgctaatacgataggctgaatgtctgaggctacca | 1860 |
| ggtttatcacataaaaaacattcagtaaaatagtaagtttctcttttcttcaggtgcatt | 1920 |
| ttcctacacctccaaatgaggaatggattttctttaatgtaagaagaatcattttttctag | 1980 |
| aggttggctttcaattctgtagcatacttggagaaactgcattatcttaaaaggcagtca | 2040 |
| aatggtgtttgtttttatcaaaatgtcaaaataacatacttggagaagtatgtaattttg | 2100 |
| tctttggaaaattacaacactgcctttgcaacactgcagttttatggtaaaataataga | 2160 |
| aatgatcgactctatcaatattgtataaaaagactgaaacaatgcatttatataatatgt | 2220 |
| atacaatattgttttgtaaataagtgtctccttttttatttactttggtatattttaca | 2280 |
| ctaaggacatttcaaattaagtactaaggcacaaagacatgtcatgcatcacagaaaagc | 2340 |
| aactactatatttcagagcaaattagcagattaaatagtggtcttaaaactccatatgt | 2400 |
| taatgattagatggttatattacaatcattttatatttttttacatgattaacattcact | 2460 |
| tatggattcatgatggctgtataaagtgaatttgaaatttcaatggtttactgtcattgt | 2520 |
| gtttaaatctcaacgttccattattttaatacttgcaaaaacattactaagtataccaaa | 2580 |
| ataattgactctattatctgaaatgaagaataaactgatgctatctcaacaataactgtt | 2640 |
| acttttattttataatttgataatgaatatttctgcatttatttacttctgttttgta | 2700 |
| aattgggattttgttaatcaaatttattgtactatgactaaatgaaattatttcttacat | 2760 |
| ctaatttgtagaaacagtataagttatattaaagtgttttcacatttttttgaaagacaa | 2820 |
| aaa | 2823 |

<SEQ ID NO: 5>
Amino acid sequence information on myostatin.
Amino acid sequence (a total of 375 amino acids)

| 1 | MQKLQLCVYIYLFMLIVAGPVDLNENSEQKENVEKEGLCNACTWRQNTKSSRIEAIKIQI | 60 |
| | LSKLRLETAPNISKDVIRQLLPKAPPLRELIDQYDVQRDDSSDGSLEDDDYHATTETIIT | 120 |
| | MPTESDFLMQVDGKPKCCFFKFSSKIQYNKVVKAQLWIYLRPVETPTTVFVQILRLIKPM | 180 |
| | KDGTRYTGIRSLKLDMNPGTGIWQSIDVKTVLQNWLKQPESNLGIEIKALDENGHDLAVT | 240 |

[SEQUENCE LISTING FREE TEXT]

```
        FPGPGEDGLNPFLEVKVTDTPKRSRRDFGLDCDEHSTESRCCRYPLTVDFEAFGWDWIIA    300

PKRYKANYCSGECEFVFLQKYPHTHLVHQANPRGSAGPCCTPTKMSPINMLYFNGKEQII    360

YGKIPAMVVDRCGCS                                                375
```

<SEQ ID NO: 6>
The sequence of primer MSTN Ex1_F1. 5'-agattcactggtgtggcaag-3'

<SEQ ID NO: 7>
The sequence of primer MSTN R2. 5'-tgcatgacatgtctttgtgc-3'

SEQUENCE LISTING

```
<110> KNC Laboratories Co., Ltd.
KOBE GAKUIN UVIVERSITY
<120> Blockage of myostatin signaling with splice-mediated variant of
myostatin
<130> FP-277PCT
<150> JP2019-37915
<151> 2019-03-01
<160> 7
<170> PatentIn version 3.5
<210> 1
<211> 251
<212> PRT
<213> Homo sapiens
<400> 1

Met Gln Lys Leu Gln Leu Cys Val Tyr Ile Tyr Leu Phe Met Leu Ile
1               5                   10                  15
Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240
```

```
Phe Pro Gly Pro Gly Glu Asp Gly Leu Asn Val
        245             250

<210> 2
<211> 1860
<212> DNA
<213> Homo sapiens
<400> 2
agattcactg gtgtggcaag ttgtctctca gactgtacat gcattaaaat tttgcttggc    60
attactcaaa agcaaaagaa aagtaaaagg aagaaacaag aacaagaaaa aagattatat   120
tgattttaaa atcatgcaaa aactgcaact ctgtgtttat atttacctgt ttatgctgat   180
tgttgctggt ccagtggatc taaatgagaa cagtgagcaa aaagaaaatg tggaaaaaga   240
ggggctgtgt aatgcatgta cttggagaca aaacactaaa tcttcaagaa tagaagccat   300
taagatacaa atcctcagta aacttcgtct ggaaacagct cctaacatca gcaaagatgt   360
tataagacaa cttttaccca agctcctcc actccgggaa ctgattgatc agtatgatgt   420
ccagagggat gacagcagcg atggctcttt ggaagatgac gattatcacg ctacaacgga   480
aacaatcatt accatgccta cagagtctga ttttctaatg caagtggatg aaaaccccaa   540
atgttgcttc tttaaattta gctctaaaat acaatacaat aaagtagtaa aggcccaact   600
atggatatat ttgagacccg tcgagactcc tacaacagtg tttgtgcaaa tcctgagact   660
catcaaacct atgaaagacg gtacaaggta tactggaatc cgatctctga aacttgacat   720
gaacccaggc actggtattt ggcagagcat tgatgtgaag acagtgttgc aaaattggct   780
caaacaacct gaatccaact taggcattga aataaaagct ttagatgaga atggtcatga   840
tcttgctgta accttcccag gaccaggaga agatgggctg aatgtctgag ctaccaggt   900 ttatcacata aaaaacattc agtaaaatag taagtttctc ttttcttcag gtgcattttc   960
ctacacctcc aaatgaggaa tggatttct taatgtaag aagaatcatt tttctagagg  1020
ttggctttca attctgtagc atacttggag aaactgcatt atcttaaaag gcagtcaaat  1080 ggtgttttgtt tttatcaaaa tgtcaaaata acatacttgg agaagtatgt aattttgtct  1140
ttggaaaatt acaacactgc ctttgcaaca ctgcagtttt tatggtaaaa taatagaaat  1200
gatcgactct atcaatattg tataaaaaga ctgaaacaat gcatttatat aatatgtata  1260
caatattgtt ttgtaaataa gtgtctcctt ttttatttac tttggtatat ttttacacta  1320
aggacatttc aaattaagta ctaaggcaca aagacatgtc atgcatcaca gaaaagcaac  1380
tacttatatt tcagagcaaa ttagcagatt aaatagtggc cttaaaactc catatgttaa  1440
tgattagatg gttatattac aatcattta tatttttta catgattaac attcacttat  1500
ggattcatga tggctgtata aagtgaattt gaaatttcaa tggtttactg tcattgtgtt  1560
taaatctcaa cgttccatta ttttaatact tgcaaaaaca ttactaagta taccaaaata  1620
attgactcta ttatctgaaa tgaagaataa actgatgcta tctcaacaat aactgttact  1680 tttatttat aatttgataa tgaatatatt tctgcattta tttacttctg ttttgtaaat  1740
tgggattttg ttaatcaaat ttattgtact atgactaaat gaaattattt cttacatcta  1800
atttgtagaa acagtataag ttatattaaa gtgttttcac attttttga aagacaaaaa  1860

<210> 3
<211> 1860
<212> DNA
<213> Artificial Sequence
<220>
<223> codon-optimized sequence
```

SEQUENCE LISTING

```
<400> 3
agattcactg gtgtggcaag ttgtctctca gactgtacat gcattaaaat tttgcttggc    60
attactcaaa agcaaaagaa aagtaaaagg aagaaacaag aacaagaaaa aagattatat   120
tgattttaaa atcatgcaga agctccagct ttgcgtgtac atctacctgt tcatgctgat   180
agttgcaggc ccagtggatc tgaatgagaa cagcgaacag aaggagaacg tagagaagga   240
aggcttgtgc aatgcctgta cttggcggca gaatacgaaa tcttcccgta ttgaggccat   300
caagatccag attctcagca aactgcgcct tgaaactgca cctaacatca gcaaggacgt   360
aatcagacag cttctgccca aagctcctcc actgagagag ctcattgacc agtacgacgt   420
ccaacgagat gacagttcag atggctcact tgaggatgac gactatcatg ccactaccga   480
aaccatcatt acaatgccga ccgaaagcga tttcctgatg caagtggatg ggaaaccaaa   540
gtgttgcttc ttcaagtttt cctccaagat ccagtacaac aaagtcgtca aggcgcaact   600
gtggatatat ctgaggcccg ttgagactcc aacaaccgtg tttgtgcaga ttttgaggct   660
gatcaagccc atgaaagacg gaacacgcta taccggaata cggagtctga aactggacat   720
gaatcccggt acagggattt ggcagtctat cgacgtcaaa acggttctcc agaactggct   780
gaaacaaccg gagtctaatc tcgggattga gatcaaggcc ttggacgaaa atggccacga   840
tctggctgtg acctttcctg gtcctggaga agatggcctg aacgtgtgag ctaccaggt    900 ttatcacata aaaaacattc agtaaaatag taagtttctc ttttcttcag gtgcattttc   960
ctacacctcc aaatgaggaa tggatttct ttaatgtaag aagaatcatt tttctagagg   1020
ttggctttca attctgtagc atacttggag aaactgcatt atcttaaaag gcagtcaaat   1080
ggtgtttgtt tttatcaaaa tgtcaaaata acatacttgg agaagtatgt aattttgtct   1140
ttggaaaatt acaacactgc ctttgcaaca ctgcagtttt tatggtaaaa taatagaaat   1200
gatcgactct atcaatattg tataaaaaga ctgaaacaat gcatttatat aatatgtata   1260
caatattgtt ttgtaaataa gtgtctcctt ttttatttac tttggtatat ttttacacta   1320
aggacatttc aaattaagta ctaaggcaca aagacatgtc atgcatcaca gaaaagcaac   1380
tacttatatt tcagagcaaa ttagcagatt aaatagtggt cttaaaactc catatgttaa   1440
tgattagatg gttatattac aatcattta tatttttta catgattaac attcacttat   1500
ggattcatga tggctgtata aagtgaattt gaaatttcaa tggtttactg tcattgtgtt   1560
taaatctcaa cgttccatta ttttaatact tgcaaaaaca ttactaagta taccaaaata   1620
attgactcta ttatctgaaa tgaagaataa actgatgcta tctcaacaat aactgttact   1680 tttatttat aatttgataa tgaatatatt tctgcattta tttacttctg ttttgtaaat   1740
tgggattttg ttaatcaaat ttattgtact atgactaaat gaaattattt cttacatcta   1800
atttgtagaa acagtataag ttatattaaa gtgttttcac attttttga aagacaaaaa   1860

<211> 2823
<212> DNA
<213> Homo sapiens
<400> 4
agattcactg gtgtggcaag ttgtctctca gactgtacat gcattaaaat tttgcttggc    60
attactcaaa agcaaaagaa aagtaaaagg aagaaacaag aacaagaaaa aagattatat   120
tgattttaaa atcatgcaaa agttgcagct gtgtgtgtac atctacctgt tcatgctgat   180
tgtcgccggt cctgttgatc tgaacgagaa ctctgagcag aaggagaacg tggagaaaga   240
```

```
aggcctgtgc aatgcttgca catggagaca gaataccaag agtagccgga tagaagccat    300
taagatccag atactgagca agctccgctt ggagacagcc cctaacattt ccaaggatgt    360
gatacggcaa cttctgccaa aggcaccacc acttagggaa ctcatcgacc agtacgacgt    420
tcagagggac gatagctccg atggctctct cgaggacgat gattaccacg ctactaccga    480
gactatcatt acaatgccta ctgagagcga ctttctgatg caagtagacg ggaaacccaa    540
gtgctgcttc ttcaaattct cctccaagat tcagtacaat aaggtcgtga agcccaact    600 ctggatctat ctccgtccgg tggaaactcc tacgaccgta ttcgtccaga ttcttaggct    660
gattaagccc atgaaagatg gaacgcggta taccggcatc agaagtttga aactggacat    720
gaatccaggt accggaatct ggcagagtat cgacgtcaaa actgtgctgc agaattggct    780
gaaacagcct gagtcaaacc tggggatcga gataaaagcg ctggatgaaa atgggcatga    840
tctggctgtc accttteegg gtcctggega agatggcctg aatcccttcc tggaagtgaa    900
agtgaccgac acacccaaac gatccagaag ggactttggc ttggattgcg acgaacactc    960
aaccgagtct cgctgttgcc gctatcctct cactgttgac tttgaggcct tggatggga   1020 ttggatcatt gctcccaagc ggtacaaagc gaactactgt tcaggggaat gcgagtttgt   1080
gttcctccag aagtatccgc atacacacct tgttcatcaa gccaatccaa gagggtctgc   1140
aggaccctgt tgtacaccca cgaagatgag ccccatcaac atgctgtatt tcaacggaaa   1200
ggaacagata atctatggca agattccagc aatggtggta gaccgatgtg gttgcagctg   1260
agatttatat taagcgttca taacttccta aaacatggaa ggttttcccc tcaacaattt   1320
tgaagctgtg aaattaagta ccacaggcta taggcctaga gtatgctaca gtcacttaag   1380
cataagctac agtatgtaaa ctaaaagggg gaatatatgc aatggttggc atttaaccat   1440
ccaaacaaat catacaagaa agttttatga tttccagagt ttttgagcta gaaggagatc   1500
aaattacatt tatgttccta tatattacaa catcggcgag gaaatgaaag cgattctcct   1560
tgagttctga tgaattaaag gagtatgctt taaagtctat ttctttaaag ttttgtttaa   1620
tatttacaga aaaatccaca tacagtattg gtaaaatgca ggattgttat ataccatcat   1680
tcgaatcatc cttaaacact tgaatttata ttgtatggta gtatacttgg taagataaaa   1740
ttccacaaaa atagggatgg tgcagcatat gcaatttcca ttcctattat aattgacaca   1800
gtacattaac aatccatgcc aacggtgcta atacgatagg ctgaatgtct gaggctacca   1860
ggtttatcac ataaaaaaca ttcagtaaaa tagtaagttt ctctttttctt caggtgcatt   1920 ttcctacacc tccaaatgag gaatggattt tctttaatgt aagaagaatc attttctag   1980 aggttggctt tcaattctgt agcatacttg gagaaactgc attatcttaa aaggcagtca   2040
aatggtgttt gttttatca aaatgtcaaa ataacatact tggagaagta tgtaattttg   2100
tctttggaaa attacaacac tgcctttgca acactgcagt ttttatggta aaataataga   2160
aatgatcgac tctatcaata ttgtataaaa agactgaaac aatgcattta tataatatgt   2220
atacaatatt gttttgtaaa taagtgtctc ctttttttatt tactttggta tattttaca   2280 ctaaggacat ttcaaattaa gtactaaggc acaaagacat gtcatgcatc acagaaaagc   2340
aactacttat atttcagagc aaattagcag attaaatagt ggtcttaaaa ctccatatgt   2400
taatgattag atggttatat tacaatcatt ttatattttt ttacatgatt aacattcact   2460 tatgattca tgatggctgt ataaagtgaa tttgaaattt caatggttta ctgtcattgt   2520
gtttaaatct caacgttcca ttatttttaat acttgcaaaa acattactaa gtataccaaa   2580
```

SEQUENCE LISTING

```
ataattgact ctattatctg aaatgaagaa taaactgatg ctatctcaac aataactgtt  2640
acttttattt tataatttga taatgaatat atttctgcat ttatttactt ctgttttgta  2700
aattgggatt ttgttaatca aatttattgt actatgacta aatgaaatta tttcttacat  2760
ctaatttgta gaaacagtat aagttatatt aaagtgtttt cactttttt tgaaagacaa   2820 aaa                                                                2823
```

<210> 5
<211> 375
<212> PRT
<213> Homo sapiens

<400> 5

```
Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
 50                  55                  60

Arg Leu Glu Thr Ala Pro Asn Ile Ser Lys Asp Val Ile Arg Gln Leu
 65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
```

SEQUENCE LISTING

```
               225                 230                 235                 240

Phe Pro Gly Pro Gly Glu Asp Gly Leu Asn Pro Phe Leu Glu Val Lys
        245                 250                 255

Val Thr Asp Thr Pro Lys Arg Ser Arg Arg Asp Phe Gly Leu Asp Cys
        260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
        325                 330                 335

Gly Pro Cys Cys Thr Pro Thr Lys Met Ser Pro Ile Asn Met Leu Tyr
        340                 345                 350

Phe Asn Gly Lys Glu Gln Ile Ile Tyr Gly Lys Ile Pro Ala Met Val
        355                 360                 365

Val Asp Arg Cys Gly Cys Ser
        370             375

<210> 6
<211> 20
<212> DNA
<213> Artificial Sequence
<220>
<223> primer
<400> 6
agattcactg gtgtggcaag     20

<210> 7
<211> 20
<212> DNA
<213> Artificial Sequence
<220>
<223> primer
<400> 7
tgcatgacat gtctttgtgc     20
```

SEQUENCE LISTING

```
<160> NUMBER OF SEQ ID NOS: 14

<210> SEQ ID NO 1
<211> LENGTH: 251
<212> TYPE: PRT
<213> ORGANISM: Homo sapiens

<400> SEQUENCE: 1

Met Gln Lys Leu Gln Leu Cys Val Tyr Ile Tyr Leu Phe Met Leu Ile
1               5                   10                  15
```

```
Val Ala Gly Pro Val Asp Leu Asn Glu Asn Ser Glu Gln Lys Glu Asn
                 20                  25                  30
Val Glu Lys Glu Gly Leu Cys Asn Ala Cys Thr Trp Arg Gln Asn Thr
             35                  40                  45
Lys Ser Ser Arg Ile Glu Ala Ile Lys Ile Gln Ile Leu Ser Lys Leu
 50                  55                  60
Arg Leu Glu Thr Ala Pro Asn Ile Ser Lys Asp Val Ile Arg Gln Leu
 65                  70                  75                  80
Leu Pro Lys Ala Pro Pro Leu Arg Glu Leu Ile Asp Gln Tyr Asp Val
                 85                  90                  95
Gln Arg Asp Asp Ser Ser Asp Gly Ser Leu Glu Asp Asp Asp Tyr His
                100                 105                 110
Ala Thr Thr Glu Thr Ile Ile Thr Met Pro Thr Glu Ser Asp Phe Leu
                115                 120                 125
Met Gln Val Asp Gly Lys Pro Lys Cys Cys Phe Phe Lys Phe Ser Ser
130                 135                 140
Lys Ile Gln Tyr Asn Lys Val Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
                180                 185                 190
Lys Leu Asp Met Asn Pro Gly Thr Gly Ile Trp Gln Ser Ile Asp Val
                195                 200                 205
Lys Thr Val Leu Gln Asn Trp Leu Lys Gln Pro Glu Ser Asn Leu Gly
                210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Val
                245                 250

<210> SEQ ID NO 2
<211> LENGTH: 1860
<212> TYPE: DNA
<213> ORGANISM: Homo sapiens

<400> SEQUENCE: 2
agattcactg gtgtggcaag ttgtctctca gactgtacat gcattaaaat tttgcttggc     60
attactcaaa agcaaagaa  aagtaaaagg aagaaacaag aacaagaaaa aagattatat    120
tgattttaaa atcatgcaaa aactgcaact ctgtgtttat atttacctgt ttatgctgat    180
tgttgctggt ccagtggatc taaatgagaa cagtgagcaa aaagaaaatg tggaaaaaga    240
ggggctgtgt aatgcatgta cttggagaca aaacactaaa tcttcaagaa tagaagccat    300
taagatacaa atcctcagta aacttcgtct ggaaacagct cctaacatca gcaaagatgt    360
tataagacaa cttttacccca agctcctcc actccgggaa ctgattgatc agtatgatgt    420
ccagagggat gacagcagcg atggctcttt ggaagatgac gattatcacg ctacaacgga    480
aacaatcatt accatgccta cagagtctga ttttctaatg caagtggatg gaaaacccaa    540
atgttgcttc tttaaattta gctctaaaat acaatacaat aaagtagtaa aggcccaact    600
atggatatat ttgagacccg tcgagactcc tacaacagtg tttgtgcaaa tcctgagact    660
catcaaacct atgaaagacg gtacaaggta tactggaatc cgatctctga acttgacat     720 gaacccaggc actggtattt ggcagagcat tgatgtgaag acagtgttgc aaaattggct    780
```

-continued

| | |
|---|---|
| caaacaacct gaatccaact taggcattga aataaaagct ttagatgaga atggtcatga | 840 |
| tcttgctgta accttcccag gaccaggaga agatgggctg aatgtctgag gctaccaggt | 900 |
| ttatcacata aaaaacattc agtaaaatag taagtttctc ttttcttcag gtgcattttc | 960 |
| ctacacctcc aaatgaggaa tggattttct taatgtaag aagaatcatt tttctagagg | 1020 |
| ttggctttca attctgtagc atacttggag aaactgcatt atcttaaaag gcagtcaaat | 1080 |
| ggtgtttgtt tttatcaaaa tgtcaaaata acatacttgg agaagtatgt aattttgtct | 1140 |
| ttggaaaatt acaacactgc ctttgcaaca ctgcagtttt tatggtaaaa taatagaaat | 1200 |
| gatcgactct atcaatattg tataaaaaga ctgaaacaat gcatttatat aatatgtata | 1260 |
| caatattgtt ttgtaaataa gtgtctcctt ttttatttac tttggtatat ttttacacta | 1320 |
| aggacatttc aaattaagta ctaaggcaca aagacatgtc atgcatcaca gaaaagcaac | 1380 |
| tacttatatt tcagagcaaa ttagcagatt aaatagtggt cttaaaactc catatgttaa | 1440 |
| tgattagatg ttatattac aatcatttta tatttttta catgattaac attcacttat | 1500 |
| ggattcatga tggctgtata agtgaatttt gaaatttcaa tggtttactg tcattgtgtt | 1560 |
| taaatctcaa cgttccatta ttttaatact tgcaaaaaca ttactaagta taccaaaata | 1620 |
| attgactcta ttatctgaaa tgaagaataa actgatgcta tctcaacaat aactgttact | 1680 |
| tttattttat aatttgataa tgaatatatt tctgcattta tttacttctg ttttgtaaat | 1740 |
| tgggattttg ttaatcaaat ttattgtact atgactaaat gaaattattt cttacatcta | 1800 |
| atttgtagaa acagtataag ttatattaaa gtgttttcac attttttga aagacaaaaa | 1860 |

<210> SEQ ID NO 3
<211> LENGTH: 1860
<212> TYPE: DNA
<213> ORGANISM: Artificial Sequence
<220> FEATURE:
<223> OTHER INFORMATION: codon-optimized sequence

<400> SEQUENCE: 3

| | |
|---|---|
| agattcactg gtgtggcaag ttgtctctca gactgtacat gcattaaaat tttgcttggc | 60 |
| attactcaaa agcaaaagaa aagtaaaagg aagaaacaag aacaagaaaa aagattatat | 120 |
| tgattttaaa atcatgcaga agctccagct ttgcgtgtac atctacctgt tcatgctgat | 180 |
| agttgcaggc ccagtggatc tgaatgaaa cagcgaacag aaggagaacg tagagaagga | 240 |
| aggcttgtgc aatgcctgta cttggcggca gaatacgaaa tcttcccgta ttgaggccat | 300 |
| caagatccag attctcagca aactgcgcct gaaactgca cctaacatca gcaaggacgt | 360 |
| aatcagacag cttctgccca aagctcctcc actgagagag ctcattgacc agtacgacgt | 420 |
| ccaacgagat gacagttcag atggctcact tgaggatgac gactatcatg ccactaccga | 480 |
| aaccatcatt acaatgccga ccgaaagcga tttcctgatg caagtggatg ggaaaccaaa | 540 |
| gtgttgcttc ttcaagtttt cctccaagat ccagtacaac aaagtcgtca aggcgcaact | 600 |
| gtggatatat ctgaggcccg ttgagactcc aacaaccgtg tttgtgcaga ttttgaggct | 660 |
| gatcaagccc atgaaagacg gaacacgcta taccggaata cggagtctga aactggacat | 720 |
| gaatcccggt acagggattt ggcagtctat cgacgtcaaa acggttctcc agaactggct | 780 |
| gaaacaaccg gagtctaatc tcgggattga gatcaaggcc ttggacgaaa atggccacga | 840 |
| tctggctgtg acctttcctg gtcctggaga agatggcctg aacgtgtgag gctaccaggt | 900 |
| ttatcacata aaaaacattc agtaaaatag taagtttctc ttttcttcag gtgcattttc | 960 |

```
ctacacctcc aaatgaggaa tggattttct ttaatgtaag aagaatcatt tttctagagg    1020
ttggctttca attctgtagc atacttggag aaactgcatt atcttaaaag gcagtcaaat    1080
ggtgtttgtt tttatcaaaa tgtcaaaata acatacttgg agaagtatgt aattttgtct    1140
ttggaaaatt acaacactgc ctttgcaaca ctgcagtttt tatggtaaaa aatagaaat     1200 gatcgactct atcaatattg tataaaaaga ctgaaacaat gcatttatat aatatgtata    1260
caatattgtt ttgtaaataa gtgtctcctt ttttatttac tttggtatat ttttacacta    1320
aggacatttc aaattaagta ctaaggcaca aagacatgtc atgcatcaca gaaaagcaac    1380
tacttatatt tcagagcaaa ttagcagatt aaatagtggt cttaaaactc catatgttaa    1440
tgattagatg gttatattac aatcatttta tatttttta catgattaac attcacttat     1500
ggattcatga tggctgtata aagtgaattt gaaatttcaa tggtttactg tcattgtgtt    1560
taaatctcaa cgttccatta ttttaatact tgcaaaaaca ttactaagta taccaaaata    1620
attgactcta ttatctgaaa tgaagaataa actgatgcta tctcaacaat aactgttact    1680
tttattttat aatttgataa tgaatatatt tctgcattta tttacttctg ttttgtaaat    1740
tgggattttg ttaatcaaat ttattgtact atgactaaat gaaattattt cttacatcta    1800
atttgtagaa acagtataag ttatattaaa gtgttttcac atttttttga aagacaaaaa    1860

<210> SEQ ID NO 4
<211> LENGTH: 2823
<212> TYPE: DNA
<213> ORGANISM: Homo sapiens

<400> SEQUENCE: 4
agattcactg gtgtggcaag ttgtctctca gactgtacat gcattaaaat tttgcttggc      60
attactcaaa agcaaaagaa aagtaaaagg aagaaacaag aacaagaaaa aagattatat     120
tgattttaaa atcatgcaaa agttgcagct gtgtgtgtac atctacctgt tcatgctgat     180
tgtcgccggt cctgttgatc tgaacgagaa ctctgagcag aaggagaacg tggagaaaga     240
aggcctgtgc aatgcttgca catggagaca gaataccaag agtagccgga tagaagccat     300
taagatccag atactgagca agctccgctt ggagacagcc cctaacattt ccaaggatgt     360
gatacggcaa cttctgccaa aggcaccacc acttagggaa ctcatcgacc agtacgacgt     420
tcagagggac gatagctccg atggctctct cgaggacgat gattaccacg ctactaccga     480
gactatcatt acaatgccta ctgagagcga ctttctgatg caagtagacg ggaaacccaa     540
gtgctgcttc ttcaaattct cctccaagat tcagtacaat aaggtcgtga agcccaact     600 ctggatctat ctccgtccgg tggaaactcc tacgaccgta ttcgtccaga ttcttaggct     660
gattaagccc atgaaagatg gaacgcggta taccggcatc agaagtttga aactggacat     720
gaatccaggt accggaatct ggcagagtat cgacgtcaaa actgtgctgc agaattggct     780
gaaacagcct gagtcaaacc tggggatcga gataaaagcg ctggatgaaa atggcatga     840 tctggctgtc acctttccgg gtcctggcga agatggcctg aatcccttcc tggaagtgaa     900
agtgaccgac acacccaaac gatccagaag ggactttggc ttggattgcg acgaacactc     960
aaccgagtct cgctgttgcc gctatcctct cactgttgac tttgaggcct tggatggga    1020 ttggatcatt gctcccaagc ggtacaaagc gaactactgt tcaggggaat gcgagtttgt    1080
gttcctccag aagtatccgc atacacacct tgttcatcaa gccaatccaa gagggtctgc    1140
aggaccctgt tgtacaccca cgaagatgag ccccatcaac atgctgtatt tcaacggaaa    1200
ggaacagata atctatggca gattccagca atggtggta gaccgatgtg gttgcagctg     1260
```

-continued

```
agatttatat taagcgttca taacttccta aaacatggaa ggttttcccc tcaacaattt    1320
tgaagctgtg aaattaagta ccacaggcta taggcctaga gtatgctaca gtcacttaag    1380
cataagctac agtatgtaaa ctaaaagggg gaatatatgc aatggttggc atttaaccat    1440
ccaaacaaat catacaagaa agttttatga tttccagagt ttttgagcta aaggagatc     1500 aaattacatt tatgttccta tatattacaa catcggcgag gaaatgaaag cgattctcct    1560
tgagttctga tgaattaaag gagtatgctt taaagtctat ttctttaaag ttttgtttaa    1620
tatttacaga aaaatccaca tacagtattg gtaaaatgca ggattgttat ataccatcat    1680
tcgaatcatc cttaaacact tgaatttata ttgtatggta gtacttggg taagataaaa     1740 ttccacaaaa atagggatgg tgcagcatat gcaatttcca ttcctattat aattgacaca    1800
gtacattaac aatccatgcc aacggtgcta atacgatagg ctgaatgtct gaggctacca    1860
ggtttatcac ataaaaaaca ttcagtaaaa tagtaagttt ctcttttctt caggtgcatt    1920
ttcctacacc tccaaatgag gaatggattt tctttaatgt aagaagaatc attttttctag   1980 aggttggctt tcaattctgt agcatacttg gagaaactgc attatcttaa aaggcagtca    2040
aatggtgttt gttttatca aaatgtcaaa ataacatact tggagaagta tgtaattttg     2100
tctttggaaa attacaacac tgcctttgca acactgcagt ttttatggta aataataga     2160 aatgatcgac tctatcaata ttgtataaaa agactgaaac aatgcattta tataatatgt    2220
atacaatatt gttttgtaaa taagtgtctc cttttttatt tactttggta tattttaca     2280 ctaaggacat ttcaaattaa gtactaaggc acaaagacat gtcatgcatc acagaaaagc    2340
aactacttat atttcagagc aaattagcag attaaatagt ggtcttaaaa ctccatatgt    2400
taatgattag atggttatat tacaatcatt ttatatttt ttacatgatt aacattcact     2460
tatggattca tgatggctgt ataaagtgaa tttgaaattt caatggttta ctgtcattgt    2520
gtttaaatct caacgttcca ttattttaat acttgcaaaa acattactaa gtataccaaa    2580
ataattgact ctattatctg aaatgaagaa taaactgatg ctatctcaac aataactgtt    2640
acttttattt tataatttga taatgaatat atttctgcat ttatttactt ctgttttgta    2700
aattgggatt ttgttaatca aatttattgt actatgacta aatgaaatta tttcttacat    2760
ctaatttgta gaaacagtat aagttatatt aaagtgtttt cacattttt tgaaagacaa     2820 aaa                                                                  2823
```

<210> SEQ ID NO 5
<211> LENGTH: 375
<212> TYPE: PRT
<213> ORGANISM: Homo sapiens

<400> SEQUENCE: 5

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
```

```
                    85                  90                  95
Gln Arg Asp Asp Ser Ser Asp Gly Ser Leu Glu Asp Asp Tyr His
            100                 105                 110
Ala Thr Thr Glu Thr Ile Ile Thr Met Pro Thr Glu Ser Asp Phe Leu
            115                 120                 125
Met Gln Val Asp Gly Lys Pro Lys Cys Cys Phe Phe Lys Phe Ser Ser
        130                 135                 140
Lys Ile Gln Tyr Asn Lys Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
            180                 185                 190
Lys Leu Asp Met Asn Pro Gly Thr Gly Ile Trp Gln Ser Ile Asp Val
            195                 200                 205
Lys Thr Val Leu Gln Asn Trp Leu Lys Gln Pro Glu Ser Asn Leu Gly
        210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
            260                 265                 270
Asp Glu His Ser Thr Glu Ser Arg Cys Cys Arg Tyr Pro Leu Thr Val
            275                 280                 285
Asp Phe Glu Ala Phe Gly Trp Asp Trp Ile Ile Ala Pro Lys Arg Tyr
        290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
            340                 345                 350
Phe Asn Gly Lys Glu Gln Ile Ile Tyr Gly Lys Ile Pro Ala Met Val
            355                 360                 365
Val Asp Arg Cys Gly Cys Ser
        370                 375

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
agattcactg gtgtggcaag                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tgcatgacat gtctttgtgc                                               20
```

```
<210> SEQ ID NO 8
<211> LENGTH: 18
<212> TYPE: DNA
<213> ORGANISM: Homo sapiens

<400> SEQUENCE: 8
gatgggctga atccgttt                                                18

<210> SEQ ID NO 9
<211> LENGTH: 18
<212> TYPE: DNA
<213> ORGANISM: Homo sapiens

<400> SEQUENCE: 9
gataggctga atgtctga                                                18

<210> SEQ ID NO 10
<211> LENGTH: 18
<212> TYPE: DNA
<213> ORGANISM: Homo sapiens

<400> SEQUENCE: 10
gatgggctga atgtctga                                                18

<210> SEQ ID NO 11
<211> LENGTH: 6
<212> TYPE: PRT
<213> ORGANISM: Homo sapiens

<400> SEQUENCE: 11

Gly Leu Asn Pro Phe Leu
1               5

<210> SEQ ID NO 12
<211> LENGTH: 18
<212> TYPE: DNA
<213> ORGANISM: Homo sapiens

<400> SEQUENCE: 12
gggctgaatc cgttttta                                                18

<210> SEQ ID NO 13
<211> LENGTH: 4
<212> TYPE: PRT
<213> ORGANISM: Homo sapiens

<400> SEQUENCE: 13

Gly Leu Asn Val
1

<210> SEQ ID NO 14
<211> LENGTH: 15
<212> TYPE: DNA
<213> ORGANISM: Homo sapiens

<400> SEQUENCE: 14
gggctgaatg tctga                                                   15
```

The invention claimed is:

1. A composition for inhibiting myostatin signaling comprising: (a) an isolated protein comprising the amino acid sequence of SEQ ID NO: 1, or (b) an isolated protein consisting of the amino acid sequence having at least 95% sequence identity with the amino acid sequence of SEQ ID NO: 1, wherein the protein is capable of inhibiting myostatin signaling; and wherein the composition is in the form of tablet, pill, granule, capsule, syrup, emulsion or suspension.

2. A composition for promoting myogenesis comprising: (a) an isolated protein comprising the amino acid sequence of SEQ ID NO: 1, or (b) an isolated protein consisting of the amino acid sequence having at least 95% sequence identity with the amino acid sequence of SEQ ID NO: 1, wherein the protein is capable of inhibiting myostatin signaling; and wherein the composition is in the form of tablet, pill, granule, capsule, syrup, emulsion or suspension.

3. A composition for increasing muscle mass in a subject having a disease in which myostatin is involved comprising: (a) an isolated protein comprising the amino acid sequence of SEQ ID NO: 1, or (b) an isolated protein consisting of the amino acid sequence having at least 95% sequence identity with the amino acid sequence of SEQ ID NO: 1, wherein the protein is capable of inhibiting myostatin signaling; wherein the composition is in the form of tablet, pill, granule, capsule, syrup, emulsion or suspension; and wherein the disease is selected from the group consisting of muscular dystrophy, spinal muscular atrophy, sarcopenia, of disuse muscle atrophy, cancer and diabetes.

4. A pharmaceutical drug comprising: (a) an isolated protein comprising the amino acid sequence of SEQ ID NO: 1, or (b) an isolated protein consisting of the amino acid sequence having at least 95% sequence identity with the amino acid sequence of SEQ ID NO: 1, wherein the protein is capable of inhibiting myostatin signaling; and wherein the composition is in the form of tablet, pill, granule, capsule, syrup, emulsion or suspension.

5. A food comprising: (a) an isolated protein comprising the amino acid sequence of SEQ ID NO: 1, or (b) an isolated protein consisting of the amino acid sequence having at least 95% sequence identity with the amino acid sequence of SEQ ID NO: 1, wherein the protein is capable of inhibiting myostatin signaling; and wherein the composition is in the form of tablet, pill, granule, capsule, syrup, emulsion or suspension.

6. A feed comprising: (a) an isolated protein comprising the amino acid sequence of SEQ ID NO: 1, or (b) an isolated protein consisting of the amino acid sequence having at least 95% sequence identity with the amino acid sequence of SEQ ID NO: 1, wherein the protein is capable of inhibiting myostatin signaling; and wherein the composition is in the form of tablet, pill, granule, capsule, syrup, emulsion or suspension.

* * * * *